(12) United States Patent
Ide et al.

(10) Patent No.: US 8,593,137 B2
(45) Date of Patent: Nov. 26, 2013

(54) EDDY CURRENT SENSOR AND EDDY CURRENT MEASUREMENT METHOD

(75) Inventors: Naotaka Ide, Toyota (JP); Takanari Yamamoto, Toyota (JP); Tatsuo Hiroshima, Kobe (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 13/696,021

(22) PCT Filed: Jun. 15, 2011

(86) PCT No.: PCT/IB2011/001340
§ 371 (c)(1),
(2), (4) Date: Nov. 2, 2012

(87) PCT Pub. No.: WO2011/158098
PCT Pub. Date: Dec. 22, 2011

(65) Prior Publication Data
US 2013/0076348 A1 Mar. 28, 2013

(30) Foreign Application Priority Data
Jun. 17, 2010 (JP) .................................. 2010-138787

(51) Int. Cl.
*G01R 33/12* (2006.01)

(52) U.S. Cl.
USPC ............ 324/232; 324/225; 324/233; 324/239

(58) Field of Classification Search
USPC ......... 324/225, 228, 229, 230, 232, 233, 239, 324/240, 243
See application file for complete search history.

(56) References Cited

U.S. PATENT DOCUMENTS

| 4,818,935 | A | * | 4/1989 | Takahashi et al. | ............ 324/232 |
| 5,311,127 | A | * | 5/1994 | Bisiaux | .................... 324/232 |
| 5,418,459 | A | * | 5/1995 | You et al. | ...................... 324/240 |
| 5,532,591 | A | * | 7/1996 | Logue | ........................... 324/242 |

(Continued)

FOREIGN PATENT DOCUMENTS

| JP | A-61-151402 | 7/1986 |
| JP | A-2002-131285 | 5/2002 |

(Continued)

OTHER PUBLICATIONS

Koyama et al., "Basic Study of Eddy Current Flaw Testing using Rotating Eddy Current," *Summary Collection of Lectures in Autumn Convention*, pp. 265-270, Oct. 1995.

(Continued)

*Primary Examiner* — Arleen M Vazquez
(74) *Attorney, Agent, or Firm* — Oliff & Berridge, PLC

(57) ABSTRACT

An eddy current sensor that includes: a probe and a computing unit. The probe has an exciting portion and a detecting portion. The exciting portion includes a first excitation coil that is wound around a non-magnetic bobbin so that a center axis direction is oriented in an x-axis direction and a second excitation coil that is wound around the non-magnetic bobbin to intersect with the first excitation coil so that a center axis direction is oriented in a y-axis direction. The detecting portion includes a detection coil that is arranged at the lower one of two intersecting portions of the first excitation coil and the second excitation coil. An eddy current measurement method for determining the thickness of a hardened layer.

8 Claims, 16 Drawing Sheets

(56) References Cited

U.S. PATENT DOCUMENTS

| | | |
|---|---|---|
| 5,548,212 A | 8/1996 | Logue |
| 6,946,833 B1 * | 9/2005 | Logue et al. .................. 324/240 |
| 2011/0163741 A1 | 7/2011 | Suzuma et al. |

FOREIGN PATENT DOCUMENTS

| | | |
|---|---|---|
| JP | A-2004-507721 | 3/2004 |
| JP | A-2004-108873 | 4/2004 |
| JP | A-2004-205212 | 7/2004 |
| JP | A-2006-100390 | 4/2006 |
| JP | A-2006-189347 | 7/2006 |
| JP | A-2007-040865 | 2/2007 |
| JP | A-2008-134106 | 6/2008 |
| JP | A-2009-031112 | 2/2009 |
| JP | A-2009-069090 | 4/2009 |
| JP | A-2009-133694 | 6/2009 |
| WO | WO 2009/139432 A1 | 11/2009 |

OTHER PUBLICATIONS

Japanese Office Action issued in Application No. 2010-138787; Dated Jan. 19, 2012 (With Translation).

* cited by examiner

EDDY CURRENT SENSOR AND EDDY CURRENT MEASUREMENT METHOD

The disclosure of Japanese Patent Application No. 2010-138787 filed on Jun. 17, 2010, including the specification, drawings and abstract is incorporated herein by reference.

BACKGROUND OF THE INVENTION

1. Field of the Invention

The invention relates to an eddy current sensor and an eddy current measurement method and, more particularly, to a technique for improving the inspection accuracy of a hardness penetration using eddy current measurement.

2. Description of Related Art

For example, a steel product (hereinafter referred to as steel product) subjected to induction quenching is used for mechanical components, such as engine parts and suspension related parts of automobiles and motorcycles. In the induction quenching, metal (conductive element) is subjected to high-frequency induction heating to be quenched. In the induction quenching of the steel product, the effective hardened layer depth and the total hardened layer depth are specified for the depth of a hardened layer after surface quenching (hereinafter, referred to as hardness penetration) and the hardness of the hardened layer. Therefore, in order to guarantee the quality of a steel product, it is necessary to measure and evaluate the hardness penetration and the hardness.

In an existing art, a sampled steel product is partially cut, the cross-sectional strength is measured by various hardness testers, such as a Vickers hardness tester, and then the hardness penetration and the hardness are evaluated on the basis of the measured result. However, a sampled steel product is discarded in this method through the destructive inspection. This leads to an increase in material cost. In addition, a period of time required for inspection elongates, and 100 percent in-line inspection is not easy, so there is a possibility that a single isolated failure cannot be detected.

Then, there is known a technique for measuring the hardness penetration and hardness of a steel product through eddy current inspection that is nondestructive inspection (for example, see Japanese Patent Application Publication No. 2009-133694 (JP-A-2009-133694) and Japanese Patent Application Publication No. 2007-40865 (JP-A-2007-40865)). In the eddy current inspection, an excitation coil through which alternating-current flows is brought close to the steel product to generate an alternating-current magnetic field, the alternating-current magnetic field is used to generate eddy current in the steel product, and then an induction magnetic field induced by the eddy current is detected by a detection coil. That is, it is possible to quantitatively measure the hardness penetration and hardness of a steel product in a short period of time in 100 percent inspection by means of the eddy current inspection without discarding the steel product. The eddy current inspection is used in not only a hardness penetration and hardness measurement test (hereinafter, referred to as hardness penetration measurement test) for measuring the hardness penetration and hardness of a steel product but also a flaw detection test for detecting a flaw, such as a crack, that arises on the surface of an inspection object, a material discrimination test for detecting foreign matter contained in an inspection object, and the like.

The steel product has a difference in magnetic permeability between a base material and a martensite that arises in a hardened layer. Thus, when the steel product is measured using an eddy current sensor, the voltage (amplitude) detected by the detection coil varies with a variation in the hardness penetration. In addition, the voltage detected by the detection coil monotonously reduces with an increase in the depth of the hardened layer. In a hardness penetration measurement test, these phenomena are used to make it possible to calculate the hardness penetration of a steel product.

For example, in the technique described in JP-A-2009-133694, an encircling coil is used to detect the hardness penetration of a shaft portion of a shaft-like component. The encircling coil is stronger in magnetic field than a probe coil (hereinafter, simply referred to as "probe coil") that has a probe formed of a coil of which the axial direction is oriented vertically with respect to a steel product to inspect the hardness penetration of the steel product, and a distance of the encircling coil to the steel product does not need to be precisely controlled, so the encircling coil is suitable for the hardness penetration measurement test. However, the inside diameter of the encircling coil, which is a measuring portion, is constant, so the filling rate of a measured portion with respect to the encircling coil (the rate of the cross-sectional area of the measured portion of the steel product with respect to the cross-sectional area of the inner circle of the encircling coil) varies with the outside diameter of the measured portion of the steel product. As the filling rate decreases, the accuracy of eddy current inspection exponentially decreases, so there is a problem in the related art that the outside diameter of the steel product varies among the measured portions and, as a result, a difference in inspection accuracy arises. In addition, the steel product that is the inspection object needs to be inserted in the encircling coil, so the application of eddy current inspection is limited to a shaft-like component having a substantially constant outside diameter. That is, it is difficult to set a component, such as a crankshaft, of which the outside diameter varies by a large amount, as an inspection object.

In addition, according to a technique described in an embodiment of JP-A-2007-40865, a probe coil is used to measure the hardness penetration of a steel product. The ratio of a detecting signal component with respect to a noise component is smaller in the hardness penetration measurement test than in another flaw detection test or a material discrimination test, so higher detection accuracy is required. However, the probe coil generates a weak magnetic field and needs to precisely control a distance to a steel product, so the probe coil may be applied to a flaw detection test or a material discrimination test but it is difficult to employ the probe coil for a hardness penetration measurement test.

In addition, when the probe coil is used to conduct hardness penetration measurement test over a steel product, a variation in output value due to a variation in the hardness penetration of the steel product and a variation in output value due to a variation in lift-off (a measuring distance of the probe coil to the steel product) are output with the same characteristic: Specifically; as shown in FIG. 16, even when the hardness penetration varies or even when the lift-off varies, variations in measured eddy current values X and Y, which are output values, appear on an X-Y coordinate plane. Therefore, the influence of the lift-off is significantly received in measuring the hardness penetration, so it is difficult to improve the measurement accuracy.

On the other hand, for example, Japanese Patent Application Publication No. 2009-69090 (JP-A-2009-69090) describes a technique for conducting eddy current inspection in such a manner that two excitation coils of which axes are oriented in a direction parallel to an inspection object surface of a steel product are arranged so as to be perpendicular to each other and a detection coil is provided at an intersecting portion of the excitation coils.

According to the technique described in JP-A-2009-69090, two excitation coils are combined so that the axes are perpendicular to each other, and the detection coil is arranged at the intersecting portion of the excitation coils. Then, alternating-current voltage is applied to the excitation coils in a state where the detection coil faces the steel product (that is, the axes of the two excitation coils are parallel to the inspection object surface of the steel product) to thereby conduct eddy current inspection.

However, the technique described in JP-A-2009-69090 is used for a flaw detection test through eddy current inspection, and it is difficult to apply the technique to a hardness penetration measurement test. That is, as described above, the ratio of a signal component with respect to a noise component is smaller in the hardness penetration measurement test than in the flaw detection test, so further higher detection accuracy is required. In addition, the flaw detection test may be determined on the basis of whether there is a flaw signal within a detection signal, whereas the hardness penetration measurement test needs to measure the magnitude of a detection signal. For these reasons, the hardness penetration measurement test more easily receives the influence of lift-off than the flaw detection test, so the configuration of a flaw detection test using eddy current inspection in the related art is not able to accurately conduct hardness penetration measurement test.

SUMMARY OF THE INVENTION

The invention provides an eddy current sensor and eddy current measurement method that are able to carry out hardness penetration measurement test with high detection accuracy even when an induction quenched component of which the outside diameter varies by a large amount is inspected, and that are able to improve measurement accuracy by eliminating the influence of lift-off in measuring a hardness penetration.

An aspect of the invention provides an eddy current sensor. The eddy current sensor includes: a probe having an exciting portion for applying a predetermined alternating-current excitation signal to a measurement object component and a detecting portion for detecting a detection signal generated in the measurement object component owing to the applied alternating-current excitation signal; and a computing unit for calculating the detection signal as a measured eddy current value. The exciting portion includes a first excitation coil that is arranged so that a center axis direction of the first excitation coil is oriented in a first axis direction and a second excitation coil that is arranged to intersect with the first excitation coil so that a center axis direction of the second excitation coil is oriented in a second axis direction perpendicular to the first axis direction, the detecting portion includes a detection coil that is arranged at one of two intersecting portions of the first excitation coil and the second excitation coil, and alternating-current voltage is applied to each of the first excitation coil and the second excitation coil as the alternating-current excitation signal in a state where the probe is arranged in proximity to the measurement object component in position such that the detection coil faces a measured portion of the measurement object component, a first magnetic field in the first axis direction and a second magnetic field in the second axis direction are generated at a portion of the measurement object component, facing the detection coil, to generate eddy currents by the magnetic fields, induced voltages generated by the eddy currents are detected by the detection coil as the detection signal, the computing unit calculates the detection signal as a measured eddy current value to thereby measure a hardness penetration of the portion of the measurement object component, facing the detection coil, on the basis of the measured eddy current value.

Another aspect of the invention provides an eddy current measurement method that uses the eddy current sensor to measure a hardness penetration of a measurement object component. The eddy current measurement method includes: a preliminary measurement step of preparing a plurality of preliminary measurement object components that have been quenched with known hardness penetrations one by one for each hardness penetration, setting a plurality of measurement distances between the eddy current sensor and each of the preliminary measurement object components at the time of quenching measurement over the preliminary measurement object components, detecting detection signals for the respective preliminary measurement object components for each measurement distance by the eddy current sensor, and calculating preliminary measured values $X0$ that serve as measured eddy current values in an X direction and preliminary measured values $Y0$ that serve as measured eddy current values in a Y direction on an X-Y coordinate plane from the detection signals for each hardness penetration and each measurement distance; a preliminary rotation step of subjecting the preliminary measured values $X0$ and the preliminary measured values $Y0$ that are detected for each hardness penetration and each measurement distance to phase rotation on the X-Y coordinate plane to calculate preliminary rotation values $X1$ corresponding to the preliminary measured values $X0$ and preliminary rotation values $Y1$ corresponding to the preliminary measured values $Y0$, and, during the phase rotation, setting a phase rotation angle so that any one of the set of preliminary rotation values $X1$ and the set of preliminary rotation values $Y1$ is substantially constant when the hardness penetration is the same; a calibration curve generating step of generating a hardness penetration calibration curve that indicates a correlation between the hardness penetration and the any one of the set of preliminary rotation values $X1$ and the set of preliminary rotation values $Y1$, which is made substantially constant in the preliminary rotation step; a measurement step of detecting a detection signal for the measurement object component by the eddy current sensor and calculating a measured eddy current value $x0$ in the X direction and a measured eddy current value $y0$ in the Y direction on the X-Y coordinate plane from the detection signal; a rotation step of subjecting the measured eddy current value $x0$ and the measured eddy current value $y0$ to phase rotation on the X-Y coordinate plane at the same phase rotation angle as that of the phase rotation angle in the preliminary rotation step to calculate a measured rotation value $x1$ corresponding to the measured eddy current value $x0$ and a measured rotation value $y1$ corresponding to the measured eddy current value $y0$; and a hardness penetration measurement step of measuring a hardness penetration of the portion of the measurement object component, facing the detection coil, from a correlation between the hardness penetration calibration curve and any one of the measured rotation value $x1$ and the measured rotation value $y1$.

In addition, in the eddy current sensor, the detecting portion may include one or two quenching determination coils that are arranged adjacent to the detection coil on one side or both sides in the first axis direction, alternating-current voltage may be applied to each of the first excitation coil and the second excitation coil as the alternating-current excitation signal in a state where the probe is arranged in proximity to the measurement object component in position such that the detection coil and each quenching determination coil face the measured portion of the measurement object component, a magnetic field in a direction perpendicular to the first axis direction and the second axis direction may be generated at a portion of the measurement object component, facing each quenching determination coil, to generate eddy current by the magnetic field, induced voltage generated by the eddy current may be detected by each quenching determination coil as a detection signal, the computing unit may calculate the detection signal of each quenching determination coil as a measured eddy current value to thereby determine whether the portion of the measurement object component, facing each quenching determination coil, is quenched or not quenched on the basis of the measured eddy current value.

Further another aspect of the invention provides an eddy current measurement method that uses the above eddy current sensor to measure a hardness penetration of a measurement object component. The eddy current measurement method includes: a preliminary quenching measurement step of preparing a plurality of preliminary quenching measurement object components that are known to be quenched or not quenched, detecting detection signals for the respective preliminary quenching measurement object components by each quenching determination coil of the eddy current sensor, and calculating the detection signals as preliminary quenching measured values for each quenching determination coil; a reference calculating step of calculating a quenching determination reference that indicates the preliminary quenching measured values for each quenching determination coil; a preliminary measurement step of preparing a plurality of preliminary measurement object components that have been quenched with known hardness penetrations one by one for each hardness penetration, setting a plurality of measurement distances between the eddy current sensor and each of the preliminary measurement object components at the time of quenching measurement over the preliminary measurement object components, detecting detection signals for the respective preliminary measurement object components for each measurement distance by the eddy current sensor, and calculating preliminary measured values $X0$ that serve as measured eddy current values in an X direction and preliminary measured values $Y0$ that serve as measured eddy current values in a Y direction on an X-Y coordinate plane from the detection signals for each hardness penetration and each measurement distance; a preliminary rotation step of subjecting the preliminary measured values $X0$ and the preliminary measured values $Y0$ that are detected for each hardness penetration and each measurement distance to phase rotation on the X-Y coordinate plane to calculate preliminary rotation values $X1$ corresponding to the preliminary measured values $X0$ and preliminary rotation values $Y1$ corresponding to the preliminary measured values $Y0$, and, during the phase rotation, setting a phase rotation angle so that any one of the set of preliminary rotation values $X1$ and the set of preliminary rotation values $Y1$ is substantially constant when the hardness penetration is the same; a calibration curve generating step of generating a hardness penetration calibration curve that indicates a correlation between the hardness penetration and the any one of the set of preliminary rotation values $X1$ and the set of preliminary rotation values $Y1$, which is made substantially constant in the preliminary rotation step; a quenching measurement step of detecting a detection signal for the measurement object component by each quenching determination coil of the eddy current sensor and calculating the detection signal as a quenching measured eddy current value for each quenching determination coil; a quenching determination step of comparing the quenching measured eddy current value and the quenching determination reference, both of which are calculated on the basis of the corresponding quenching determination coil, to determine whether the portion of the measurement object component, facing each quenching determination coil, is quenched or not quenched; a measurement step of detecting a detection signal by the eddy current sensor in the measurement object component that is determined in the quenching determination step that all quenching determination portions are quenched and calculating a measured eddy current value $x0$ in the X direction and a measured eddy current value $y0$ in the Y direction on the X-Y coordinate plane from the detection signal; a rotation step of subjecting the measured eddy current value $x0$ and the measured eddy current value $y0$ to phase rotation on the X-Y coordinate plane at the same phase rotation angle as that of the phase rotation angle in the preliminary rotation step to calculate a measured rotation value $x1$ corresponding to the measured eddy current value $x0$ and a measured rotation value $y1$ corresponding to the measured eddy current value $y0$; and a hardness penetration measurement step of measuring a hardness penetration of the portion of the measurement object component, facing the detection coil, from a correlation between the hardness penetration calibration curve and any one of the measured rotation value $x1$ and the measured rotation value $y1$.

In addition, in the eddy current sensor, the detecting portion may include one or two perpendicular quenching determination coils, each of which is arranged perpendicularly to each quenching determination coil on an opposite side of the corresponding quenching determination coil with respect to the detection coil, alternating-current voltage may be applied to each of the first excitation coil and the second excitation coil as the alternating-current excitation signal in a state where the probe is arranged in proximity to the measurement object component in position such that the detection coil and each quenching determination coil face the measured portion of the measurement object component and each perpendicular quenching determination coil faces an upright portion that is perpendicular to the measured portion of the measurement object component to generate a magnetic field in the first axis direction at the upright portion of the measurement object component to thereby generate eddy current by the magnetic field, induced voltage generated by the eddy current may be detected by each perpendicular quenching determination coil as a detection signal, the computing unit may calculate the detection signal of each quenching determination coil and the detection signal of each perpendicular quenching determination coil as measured eddy current values to determine whether the portions of the measurement object component, respectively facing each quenching determination coil and each perpendicular quenching determination coil, is quenched or not quenched on the basis of the measured eddy current values.

Yet another aspect of the invention provides an eddy current measurement method that uses the above eddy current sensor to measure a hardness penetration of a measurement object component. The eddy current measurement method includes: a preliminary quenching measurement step of preparing a plurality of preliminary quenching measurement object components, each of which has a measured portion and an upright portion perpendicular to the measured portion and is known to be quenched or not quenched, detecting detection signals at the measured portion and upright portion of each preliminary quenching measurement object component by each quenching determination coil and each perpendicular quenching determination coil of the eddy current sensor, and calculating the detection signals as preliminary quenching measured values for each quenching determination coil and each perpendicular quenching determination coil; a reference calculating step of calculating a quenching determination reference that indicates the preliminary quenching measured values for each quenching determination coil and each perpendicular quenching determination coil; a preliminary measurement step of preparing a plurality of preliminary measurement object components that have been quenched with known hardness penetrations one by one for each hardness penetration; setting a plurality of measurement distances between the eddy current sensor and each of the preliminary measurement object components at the time of quenching measurement over the preliminary measurement object components, detecting detection signals for the respective preliminary measurement object components for each measurement distance by the eddy current sensor, and calculating preliminary measured values X0 that serve as measured eddy current values in an X direction and preliminary measured values Y0 that serve as measured eddy current values in a Y direction on an X-Y coordinate plane from the detection signals for each hardness penetration and each measurement distance; a preliminary rotation step of subjecting the preliminary measured values X0 and the preliminary measured values Y0 that are detected for each hardness penetration and each measurement distance to phase rotation on the X-Y coordinate plane to calculate preliminary rotation values X1 corresponding to the preliminary measured values X0 and preliminary rotation values Y1 corresponding to the preliminary measured values Y0, and, during the phase rotation, setting a phase rotation angle so that any one of the set of preliminary rotation values X1 and the set of preliminary rotation values Y1 is substantially constant when the hardness penetration is the same; a calibration curve generating step of generating a hardness penetration calibration curve that indicates a correlation between the hardness penetration and the any one of the set of preliminary rotation values X1 and the set of preliminary rotation values Y1, which is made substantially constant in the preliminary rotation step; a quenching measurement step of detecting a detection signal at the measured portion of the measurement object component by each quenching determination coil of the eddy current sensor and calculating the detection signal as a quenching measured eddy current value for each quenching determination coil; a perpendicular quenching measurement step of detecting a detection signal at each upright portion of the measurement object component by each perpendicular quenching determination coil of the eddy current sensor and calculating the detection signal as a perpendicular quenching measured eddy current value for each perpendicular quenching determination coil; a quenching determination step of comparing the quenching measured eddy current value and the quenching determination reference, both of which are calculated on the basis of the corresponding quenching determination coil, and comparing the perpendicular quenching measured eddy current value and the quenching determination reference, both of which are calculated on the basis of the corresponding perpendicular quenching determination coil, to determine whether the measured portion and upright portion of the measurement object component are quenched or not quenched; a measurement step of detecting a detection signal by the eddy current sensor in the measurement object component that is determined in the quenching determination step that all the measured portions and upright portions are quenched and calculating a measured eddy current value x0 in the X direction and a measured eddy current value y0 in the Y direction on the X-Y coordinate plane from the detection signal; a rotation step of subjecting the measured eddy current value x0 and the measured eddy current value y0 to phase rotation at the same phase rotation angle as that of the phase rotation in the preliminary rotation step to calculate a measured rotation value x1 and a measured rotation value y1; and a hardness penetration measurement step of measuring a hardness penetration of the portion of the measurement object component, facing the detection coil, from a correlation between the hardness penetration calibration curve and any one of the measured rotation value x1 and the measured rotation value y1.

Yet further another aspect of the invention provides an eddy current sensor. The eddy current sensor includes: a probe having an exciting portion for applying a predetermined alternating-current excitation signal to a measurement object component and a detecting portion for detecting a detection signal generated in the measurement object component owing to the applied alternating-current excitation signal; and a computing unit for calculating the detection signal as a measured eddy current value, and the eddy current sensor is formed in a prismatic shape of which an axis is oriented in a first axis direction. The exciting portion includes a first excitation coil that is wound so that a center axis direction of the first excitation coil is oriented in the first axis direction, a second excitation coil that is wound to intersect with the first excitation coil so that a center axis direction of the second excitation coil is oriented in a second axis direction perpendicular to the first axis direction, and a third excitation coil and a fourth excitation coil that are wound to intersect with the first excitation coil so that center axes directions of the third excitation coil and fourth excitation coil are oriented in directions perpendicular to the first axis direction and inclined equally with respect to the second axis direction, the detecting portion includes a first detection coil that is arranged at one of two intersecting portions of the first excitation coil and the second excitation coil, a second detection coil that is arranged at one of two intersecting portions of the first excitation coil and the third excitation coil, adjacent to the first detection coil, and a third detection coil that is arranged at one of two intersecting portions of the first excitation coil and the fourth excitation coil, adjacent to the first detection coil, and alternating-current voltage is applied to each of the first excitation coil, the second excitation coil, the third excitation coil and the fourth excitation coil as the alternating-current excitation signal in a state where the probe is arranged in proximity to the measurement object component in position such that the first detection coil faces a measured portion of the measurement object component to generate magnetic fields in the measurement object component to thereby generate eddy currents by the magnetic fields, induced voltages generated by the eddy currents are detected by the first detection coil, the second detection coil and the third detection coil as detection signals, the computing unit calculates the detection signals as measured eddy current values to thereby measure hardness penetrations of the portions of the measurement object component, respectively facing the first, second and third detection coils, on the basis of the measured eddy current values.

Another aspect of the invention provides an eddy current measurement method that uses the eddy current sensor to measure a hardness penetration of a measurement object component. The eddy current measurement method includes: a preliminary measurement step of preparing a plurality of preliminary measurement object components that have been quenched with known hardness penetrations one by one for each hardness penetration, setting a plurality of measurement distances between the eddy current sensor and each of the preliminary measurement object components at the time of quenching measurement over the preliminary measurement object components, detecting detection signals for the respective preliminary measurement object components for each measurement distance by the eddy current sensor, and calculating preliminary measured values X0 that serve as measured eddy current values in an X direction and preliminary measured values Y0 that serve as measured eddy current values in a Y direction on an X-Y coordinate plane from the detection signals for each hardness penetration and each measurement distance; a preliminary rotation step of subjecting the preliminary measured values X0 and the preliminary measured values Y0 that are detected for each hardness penetration and each measurement distance to phase rotation on the X-Y coordinate plane to calculate preliminary rotation values X1 corresponding to the preliminary measured values X0 and preliminary rotation values Y1 corresponding to the preliminary measured values Y0, and, during the phase rotation, setting a phase rotation angle so that any one of the set of preliminary rotation values X1 and the set of preliminary rotation values Y1 is substantially constant when the hardness penetration is the same; a calibration curve generating step of generating a hardness penetration calibration curve that indicates a correlation between the hardness penetration and the any one of the set of preliminary rotation values X1 and the set of preliminary rotation values Y1, which is made substantially constant in the preliminary rotation step; a first measurement step of detecting a detection signal for the measurement object component by the first detection coil of the eddy current sensor and calculating a first measured eddy current value x01 in the X direction and a first measured eddy current value y01 in the Y direction on the X-Y coordinate plane from the detection signal; a second measurement step of detecting a detection signal for the measurement object component by the second detection coil of the eddy current sensor and calculating a second measured eddy current value x02 in the X direction and a second measured eddy current value y02 in the Y direction on the X-Y coordinate plane from the detection signal; a third measurement step of detecting a detection signal for the measurement object component by the third detection coil of the eddy current sensor and calculating a third measured eddy current value x03 in the X direction and a third measured eddy current value y03 in the Y direction on the X-Y coordinate plane from the detection signal; a rotation step of subjecting the first measured eddy current value x01, the first measured eddy current value y01, the second measured eddy current value x02, the second measured eddy current value y02, the third measured eddy current value x03 and the third measured eddy current value y03 to phase rotation at the same phase rotation angle as that of the phase rotation in the preliminary rotation step to calculate a first measured rotation value x11, a first measured rotation value y11, a second measured rotation value x12, a second measured rotation value y12, a third measured rotation value x13 and a third measured rotation value y13 corresponding to the respective measured eddy current values; a first hardness penetration measurement step of measuring a hardness penetration of a portion of the measurement object component, facing the first detection coil, from a correlation between the hardness penetration calibration curve and any one of the first measured rotation value x11 and the first measured rotation value y11; a second hardness penetration measurement step of measuring a hardness penetration of a portion of the measurement object component, facing the second detection coil, from a correlation between the hardness penetration calibration curve and any one of the second measured rotation value x12 and the second measured rotation value y12; and a third hardness penetration measurement step of measuring a hardness penetration of a portion of the measurement object component, facing the third detection coil, from a correlation between the hardness penetration calibration curve and any one of the third measured rotation value x13 and the third measured rotation value y13.

Further another aspect of the invention provides an eddy current sensor. The eddy current sensor includes: a probe having an exciting portion for applying a predetermined alternating-current excitation signal to a hollow measurement object component and a detecting portion for detecting a detection signal generated in the measurement object component owing to the applied alternating-current excitation signal; and a computing unit for calculating the detection signal as a measured eddy current value. The exciting portion includes a first excitation coil that is arranged so that a center axis direction of the first excitation coil is oriented in a first axis direction and a second excitation coil that is arranged to intersect with the first excitation coil so that a center axis direction of the second excitation coil is oriented in a second axis direction perpendicular to the first axis direction, the detecting portion includes two detection coils that are arranged at both intersecting portions of the first excitation coil and the second excitation coil, and alternating-current voltage is applied to each of the first excitation coil and the second excitation coil as the alternating-current excitation signal in a state where the probe is arranged in proximity to the hollow measurement object component in position such that the probe is inserted in the hollow measurement object component and the detection coils each face an inner peripheral surface of the hollow measurement object component to generate a first magnetic field in the first axis direction and a second magnetic field in the second axis direction at portions of the hollow measurement object component, facing the respective detection coils, to thereby generate eddy currents in the measurement object component by the magnetic fields, induced voltages generated by the eddy currents are detected by the detection coils as detection signals, the computing unit calculates the detection signals as measured eddy current values to measure hardness penetrations of the portions of the measurement object component, respectively facing the detection coils, on the basis of the measured eddy current values.

The following advantageous effects may be obtained from the aspects of the invention. According to the aspects of the invention, it is possible to carry out hardness penetration measurement test with high detection accuracy even when an induction quenched component of which the outside diameter varies by a large amount is inspected, and it is possible to improve measurement accuracy by eliminating the influence of lift-off in measuring a hardness penetration.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Hereinafter, an embodiment of the invention will be described. Note that the technical scope of the invention is not limited to the following embodiments but it widely encompasses all the scope of the technical idea that becomes apparent from the content described in the specification and the drawings and that is truly intended by the invention.

The aspect of the invention intends to expand the application range of eddy current measurement in such a manner that an eddy current sensor includes a plurality of excitation coils, which serve as exciting portions, and a plurality of detection coils, which serve as detecting portions, and an arranging method, coupling method, and the like, of these coils are devised. Hereinafter, the embodiment of the invention will be described. Note that, in the embodiments of the invention, the case where eddy current measurement using an eddy current sensor is used to detect the quenching quality (hardness penetration, quenched hardness) of a quenched component through induction quenching, or the like, will be mainly described as an example. That is, the quenching quality of a quenched component, which is a measurement object component, is inspected by conducting eddy current measurement using an eddy current sensor.

Figure 1:
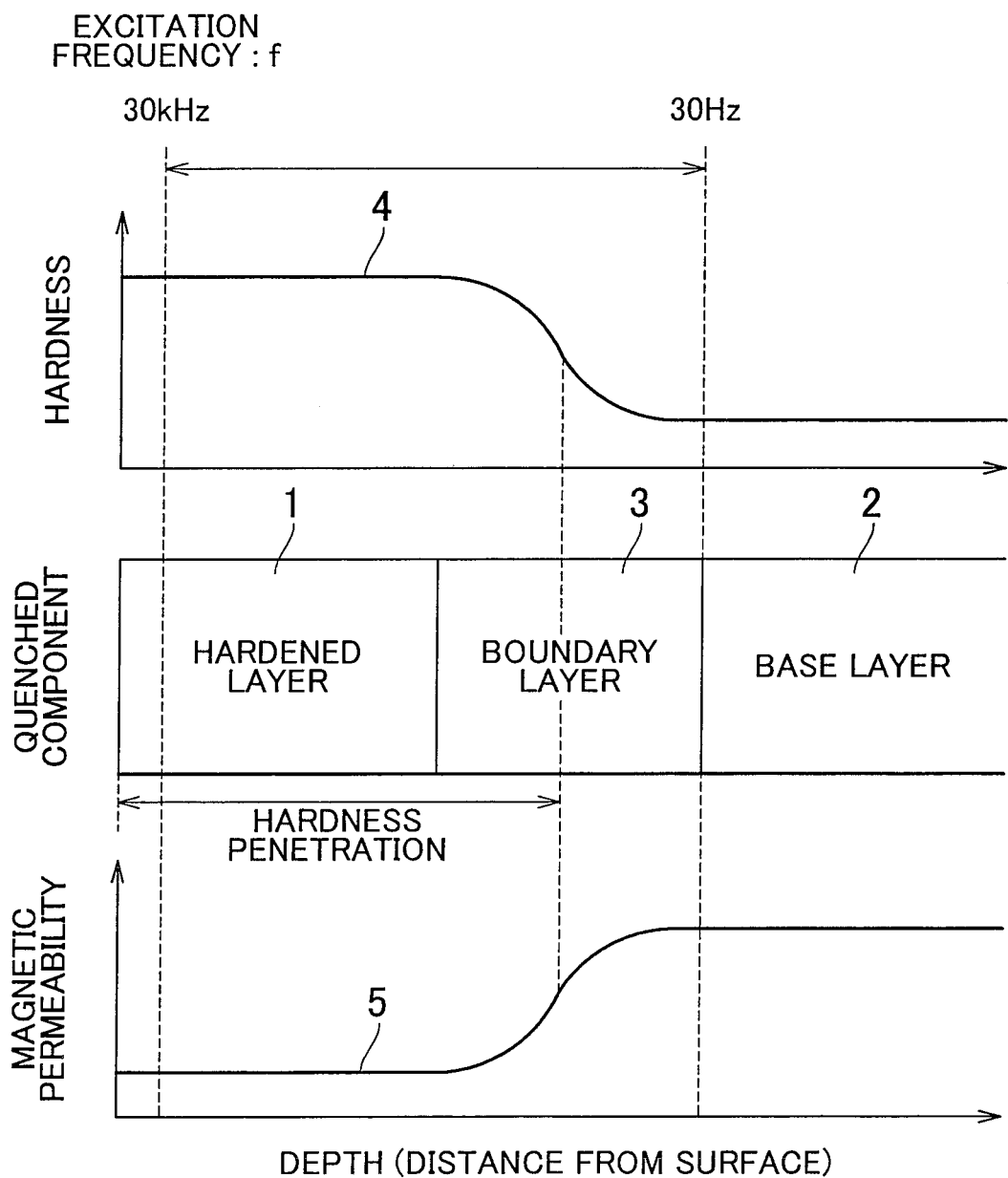
FIG. 1 is a graph that shows the correlation among the state of a layer, hardness and magnetic permeability of a quenched component in the depth direction.

FIG. 1 is a graph that shows the correlation among the state of a layer, hardness and magnetic permeability of a quenched component, which is a steel product (S45C, or the like) subjected to quenching, in the direction of depth (distance from the surface). As shown in FIG. 1, in the quenched component, a hardened layer 1 and a base layer 2 are formed in order from the surface side via a boundary layer 3 as the schematic texture configuration of the quenched component. The hardened layer 1 is a portion that has been subjected to quenching. The base layer 2 is a base material portion. By referring to a hardness change curve 4, the hardened layer 1 and the base layer 2 have different hardnesses, and the hardness of the hardened layer 1 is higher than that of the base layer 2. In the boundary layer 3, the hardness gradually reduces from a side adjacent to the hardened layer 1 toward the base layer 2. A specific example of the hardness in Vickers hardness (Hv) is such that the hardened layer 1 has a hardness of 600 to 700 Hv, and the base layer 2 has a hardness of about 300 Hv.

On the other hand, by referring to a magnetic permeability change curve 5, a variation in magnetic permeability against a distance from the surface of the quenched component is substantially inversely proportional to a variation in hardness against a distance from the surface of the quenched component. That is, the magnetic permeability of the hardened layer 1 is lower than that of the base layer 2, and gradually increases in the boundary layer 3 from a side adjacent to the hardened layer 1 toward the base layer 2. In the eddy current measurement according to the present embodiment, the correlation between a hardness and a magnetic permeability of the quenched component against a distance from the surface is utilized.

Figure 2:
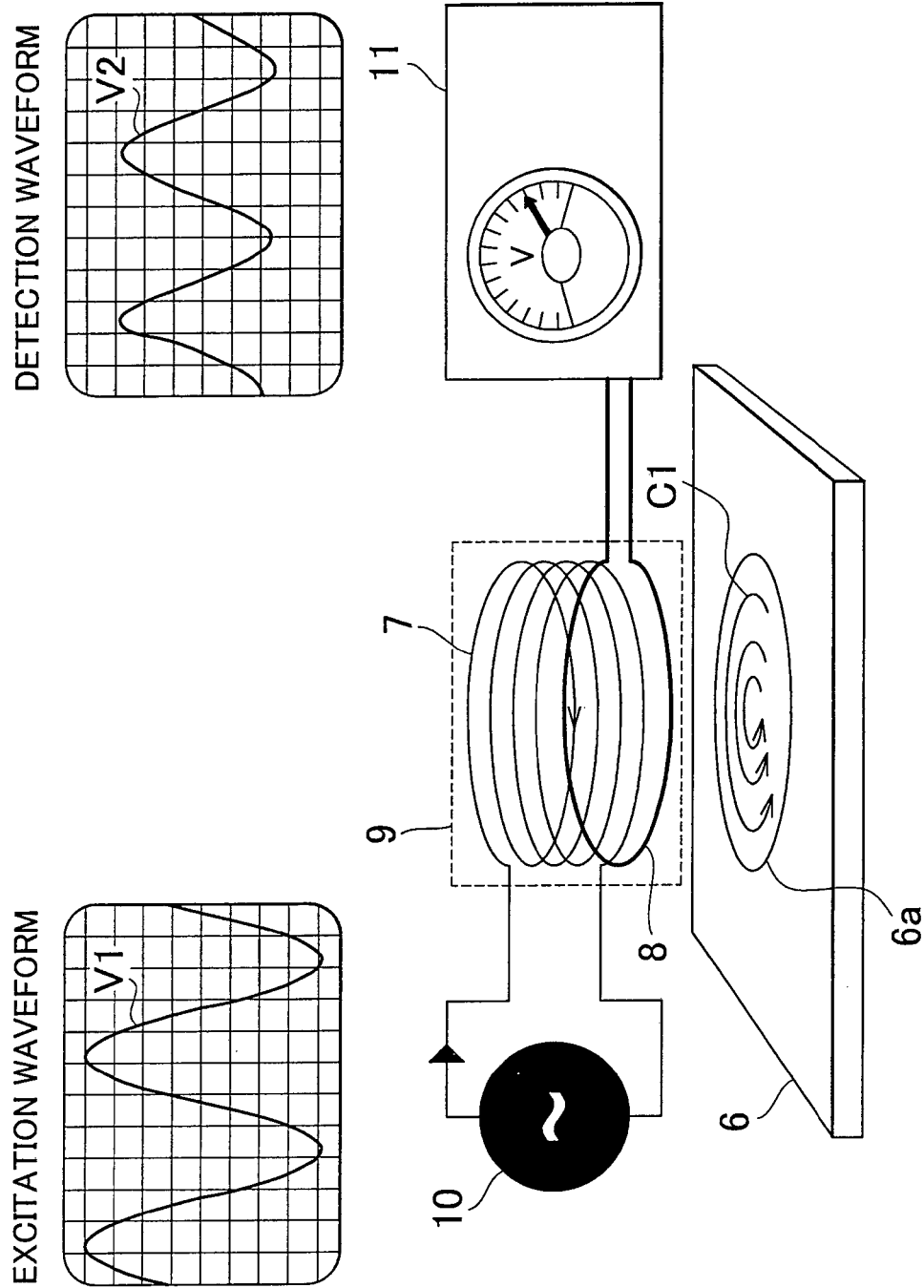
FIG. 2 is a schematic view that shows the system configuration for conducting eddy current measurement according to an embodiment.

The schematic system configuration (principle of measurement) for carrying out eddy current measurement according to the present embodiment will be described with reference to FIG. 2. As shown in FIG. 2, in the eddy current measurement, an eddy current sensor 9 having an excitation coil 7, which serves as an exciting portion, and a detection coil 8, which serves as a detecting portion, is set at a predetermined position with respect to a measured portion 6a of a work piece (magnetic material) 6, which is a measurement object component. In the above configuration, as the excitation coil 7 is supplied with electric current, a magnetic field appears around the excitation coil 7. Then, eddy current is generated in the work piece 6, which is the magnetic material, near the surface of the measured portion 6a of the work piece 6 through electromagnetic induction (see the arrow C1 in FIG. 2). As the eddy current is generated at the surface of the measured portion 6a, a magnetic flux penetrates through the detection coil 8, and then induced voltage is generated in the detection coil 8. Then, the induced voltage is measured by the detection coil 8.

Both ends (both terminals) of the excitation coil 7 are connected to an alternating-current power supply 10. The alternating-current power supply 10 applies a predetermined alternating-current excitation signal (exciting alternating-current voltage signal) V1 to the excitation coil 7. Both ends (both terminals) of the detection coil 8 are connected to a measurement device 11. The measurement device 11 detects the magnitude of a detection signal (a voltage signal regarding the induced voltage) V2 obtained from the detection coil 8 when the alternating-current excitation signal V1 is applied from the alternating-current power supply 10 to the excitation coil 7 and a phase difference (phase delay) Φ (see FIG. 3) of the detection signal V2 with respect to the alternating-current excitation signal V1. Here, in order to detect the phase difference Φ, the measurement device 11 is supplied with the alternating-current excitation signal V1 (waveform) as an amplified phase detection signal.

Figure 3:
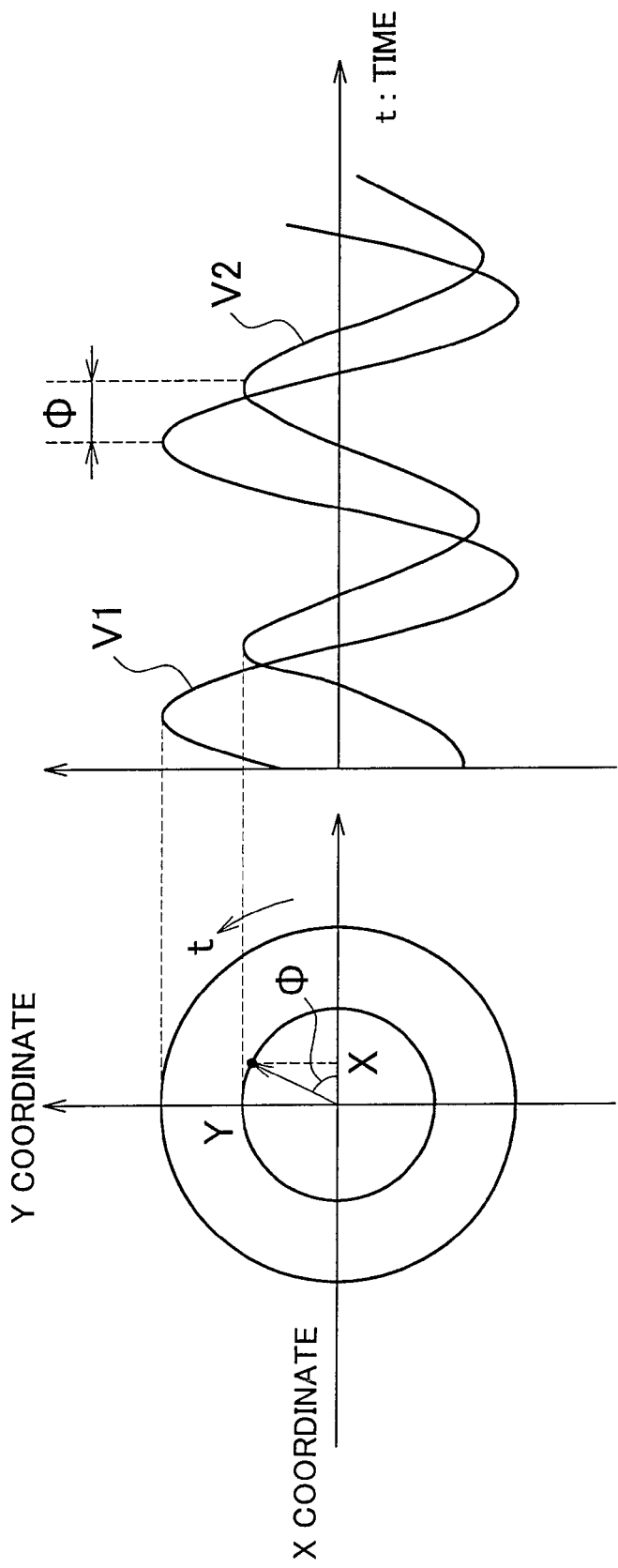
FIG. 3 is a graph that shows the relationship between an alternating-current excitation signal and a detection signal in eddy current measurement.

The detection signal V2 detected by the detection coil 8 reflects the magnetic permeability of the measured portion 6a (work piece 6). That is, as the magnetic permeability of the measured portion 6a increases, a magnetic flux attended with generation of eddy current as described above increases, so the magnitude of the detection signal V2 increases. Conversely, as the magnetic permeability of the measured portion 6a decreases, a magnetic flux attended with generation of eddy current reduces, so the magnitude of the detection signal V2 decreases. In order to quantify (digitize) the detection signal V2 based on the eddy current, as shown in FIG. 3, an amplitude value Y that is a value of the magnitude of the detection signal V2 and a value X (=Y cos Φ) that is a value based on the phase difference Φ of the detection signal V2 with respect to the alternating-current excitation signal V1 are focused, and the following findings are known.

First, the amplitude value Y of the detection signal V2 may correlate with the quenched surface hardness (hardness of a quenched portion). That is, as is apparent from a comparison between the hardness change curve 4 and the magnetic permeability change curve 5 shown in FIG. 1, there is a correlation that the magnetic permeability increases as the quenched surface hardness decreases. As the magnetic permeability increases, a magnetic flux generated when the alternating-current excitation signal V1 is applied to the excitation coil 7 increases, so eddy current induced at the surface of the measured portion 6a also increases. In accordance with this, the amplitude value Y of the detection signal V2 detected by the detection coil 8 also increases. Thus, conversely, a magnetic flux that penetrates through the measured portion 6a at which eddy current is generated, that is, a magnetic permeability, is derived from the amplitude value Y of the detection signal V2 detected by the detection coil 8. By so doing, the quenched surface hardness is obtained from the correlation between the hardness change curve 4 and the magnetic permeability change curve 5 that are shown in FIG. 1.

Next, the value X based on the phase difference Φ of the detection signal V2 with respect to the alternating-current excitation signal V1 may correlate with the quench depth (the depth of a quench-hardened layer). That is, an increase in the quench depth, that is, an increase in the quenched hardened layer 1 in the quenched component, means an increase in the low magnetic permeability range in the depth direction, so the phase delay of the detection signal V2 with respect to the alternating-current excitation signal V1 increases. Thus, the degree of the quench depth is obtained from the magnitude of the value based on the phase difference Φ.

In the eddy current measurement for inspecting the quenching quality of a quenched component on the basis of the above principle of measurement, the eddy current sensor having the excitation coil and the detection coil are used as described above. Hereinafter, the configuration of the eddy current sensor will be described as the embodiments of the invention.

First, an eddy current sensor according to a first embodiment of the invention will be described with reference to FIG. 4A to FIG. 5B. Note that, in the specification, the arrows in each drawing respectively indicate an x-axis direction, a y-axis direction and a z-axis direction.

Figure 4A:
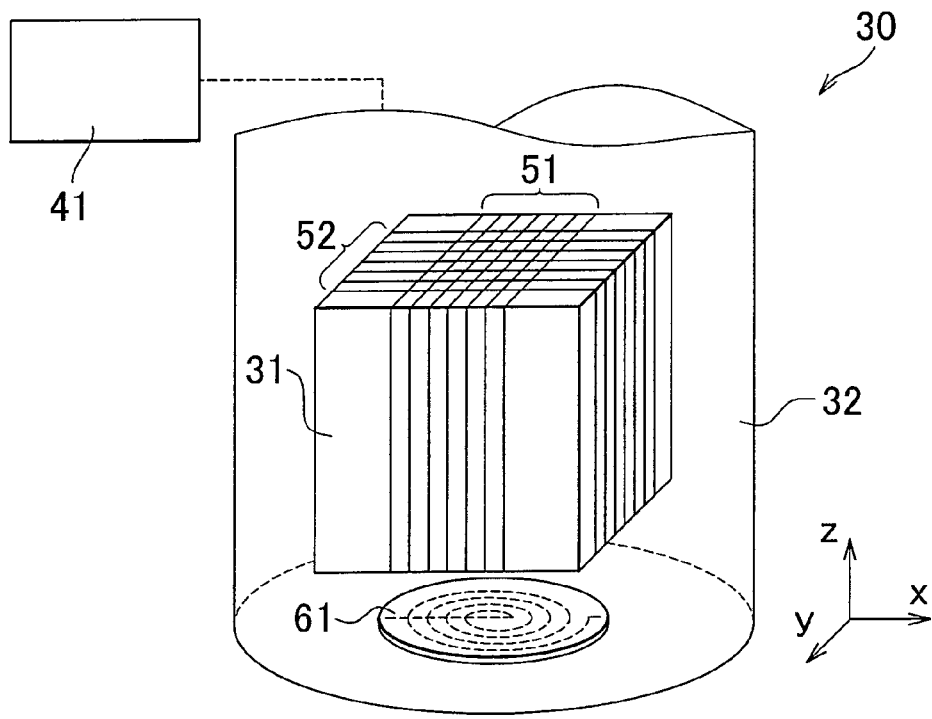
FIG. 4A is a schematic view that shows the configuration of an eddy current sensor according to a first embodiment.
Figure 4B:
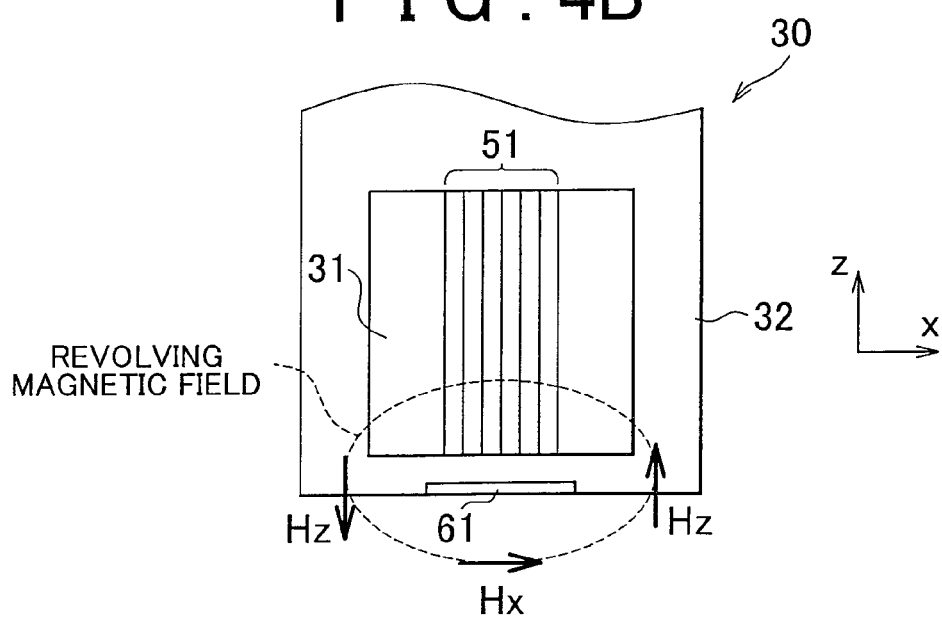
FIG. 4B is a side view of the eddy current sensor according to the first embodiment.

As shown in FIG. 4A and FIG. 4B, the eddy current sensor according to the present embodiment includes a probe 30 and a computing unit 41. The probe 30 includes an exciting portion and a detecting portion that are accommodated in a case 32. As described above, the exciting portion is applied with a predetermined alternating-current excitation signal (see the alternating-current excitation signal V1) in a state where the exciting portion is arranged to face a measurement object component. The detecting portion detects a detection signal (see the above detection signal V2) generated by eddy current that is generated in the measurement object component by the exciting portion to which the alternating-current excitation signal, is applied. In addition, the computing unit 41 is electrically connected to a detection coil 61 (described later), and calculates the detection signal as a measured eddy current value.

The exciting portion is formed so that a first excitation coil 51 and a second excitation coil 52 are wound around a substantially cubular non-magnetic bobbin 31. Specifically, the first excitation coil 51 is wound around the non-magnetic bobbin 31 so that the center axis direction is oriented in the x-axis direction that is a first axis direction. In addition, the second excitation coil 52 is wound around the non-magnetic bobbin 31 to intersect with the first excitation coil 51 so that the center axis direction is oriented in the y-axis direction that is a second axis direction perpendicular to the first axis direction. In other words, the first excitation coil 51 and the second excitation coil 52 are arranged so as to intersect at right angles with each other on the top surface and bottom surface of the non-magnetic bobbin 31. Both ends (both terminals) of each of the first excitation coil 51 and the second excitation coil 52 are connected to the alternating-current power supply (not shown). That is, the first excitation coil 51 and the second excitation coil 52 are excitation coils for applying a predetermined alternating-current excitation signal to the measurement object component.

The detecting portion includes the detection coil 61 that is arranged at the lower one of two intersecting portions of the first excitation coil 51 and the second excitation coil 52. The detection coil 61 is arranged at a substantially center portion of the lower-side intersecting portion of the first excitation coil 51 and the second excitation coil 52 in an X-Y plane (bottom surface of the non-magnetic bobbin 31). In the present embodiment, a thin-film planar coil is used as the detection coil 61; instead, another coil, such as a pancake coil, may also be used. Both ends (both terminals) of the detection coil 61 are connected to a measurement device (not shown) of the computing unit 41. That is, the detection coil 61 detects a detection signal, generated by eddy currents, from the measurement object component to which the alternating-current excitation signal is applied.

Figure 5A:
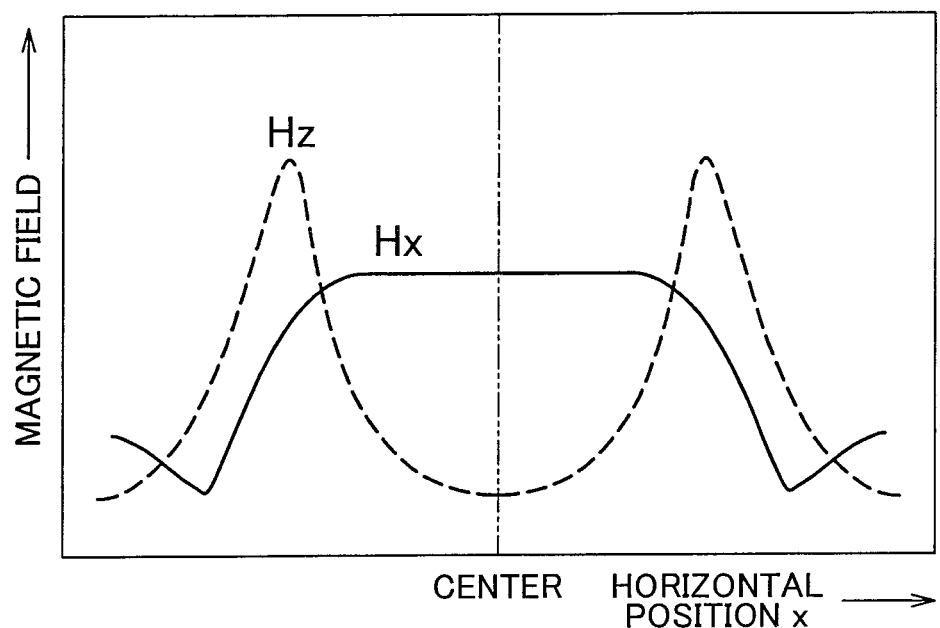
FIG. 5A is a graph that shows a magnetic field distribution generated in the eddy current sensor according to the first embodiment.

When the thus configured eddy current sensor is used to measure the hardness penetration of the measurement object component, voltage is applied to each of the first excitation coil 51 and the second excitation coil 52 by the alternating-current power supply in a state where the probe 30 is arranged in proximity to the measurement object component in position such that the detection coil 61 faces a measured portion of the measurement object component. That is, when the hardness penetration is measured, the first excitation coil 51 and the second excitation coil 52 are arranged so that the center axes of the first excitation coil 51 and second excitation coil 52 are parallel to the surface of the measured portion of the measurement object component. At the moment at which current flows through the first excitation coil 51, a revolving magnetic field is generated around the first excitation coil 51 in accordance with the corkscrew rule as shown in FIG. 4B. At this time, as shown in FIG. 4B, a horizontal magnetic field Hx in the x-axis direction is strongly generated around the center portion of the probe 30, and a vertical magnetic field in the z-axis direction is strongly generated around both end portions of the probe 30. More specifically, as shown in FIG. 5A, in terms of the horizontal position x of the probe 30, the horizontal magnetic field Hx becomes strong around the center portion, and the vertical magnetic field Hz becomes strong around both end portions.

Figure 5B:
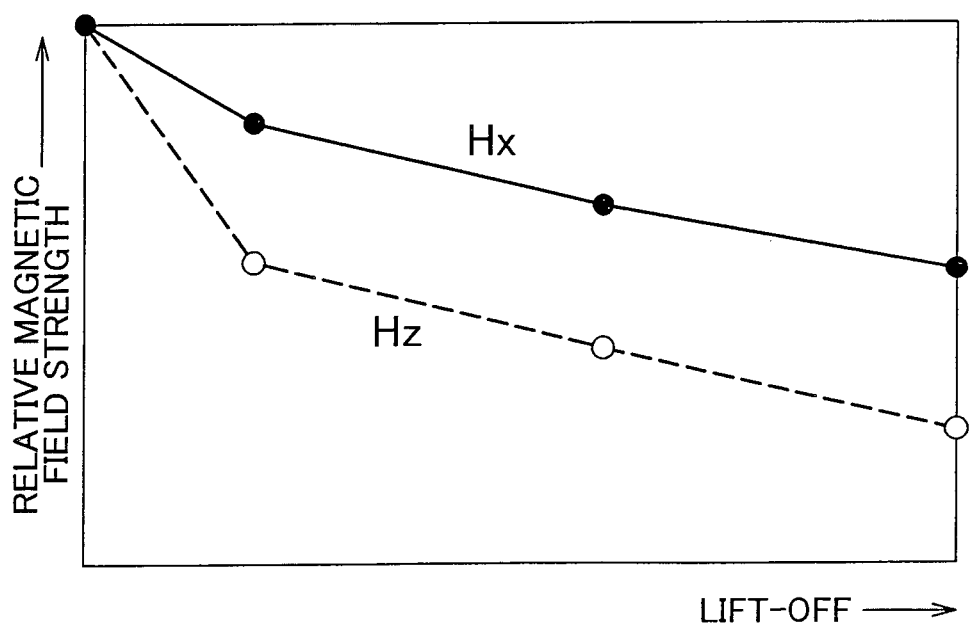
FIG. 5B is a graph that shows a relative variation in magnetic field strength generated in the eddy current sensor according to the first embodiment.

The horizontal magnetic field Hx has such a feature that the attenuation of a relative magnetic field strength resulting from a variation in lift-off (a measurement distance of the eddy current sensor to the measurement object component, that is, a distance between the measurement object component and the eddy current sensor at the time of measurement) is smaller than that of the vertical magnetic field Hz. Specifically, as shown in FIG. 5B, the attenuation of the magnetic field strength when the lift-off is large is smaller in the vertical magnetic field Hz than in the horizontal magnetic field Hx. That is, eddy current measurement is less influenced by lift-off when the horizontal magnetic field Hx is used.

Thus, in the present embodiment, among magnetic fields generated by the first excitation coil 51, the horizontal magnetic field Hx that is generated in the x-axis direction as a first magnetic field (among magnetic fields generated by the second excitation coil 52, the horizontal magnetic field Hy that is generated in the y-axis direction as a second magnetic field) is used for eddy current measurement. That is, the horizontal magnetic field Hx and the horizontal magnetic field Hy are generated at a portion of the measurement object component, facing the detection coil 61. Then, electromagnetic induction is caused by the horizontal magnetic field Hx and the horizontal magnetic field Hy to generate eddy currents in the measurement object component that is a magnetic material. Furthermore, with the generation of eddy current at the surface of the measurement object component, a magnetic flux is caused to pass through the detection coil 61 to thereby generate induced voltage in the detection coil 61. Then, the induced voltage is measured as a detection signal by the detection coil 61. Then, the computing unit 41 calculates the detection signal as a measured eddy current value, and then measures the hardness penetration of the portion of the measurement object component, facing the detection coil 61, on the basis of the measured eddy current value.

In the present embodiment, as described above, the horizontal magnetic field of which the attenuation of the magnetic field strength due to lift-off is small is used for eddy current measurement, so the hardness penetration measurement test is less influenced by lift-off. That is, even in the hardness penetration measurement test in which it is necessary to measure the magnitude of a detection signal and the ratio of a detected signal component with respect to a noise component is small and, as a result, higher detection accuracy is required, the hardness penetration measurement test is less influenced by lift-off, so it is possible to accurately conduct eddy current measurement.

Figure 6:
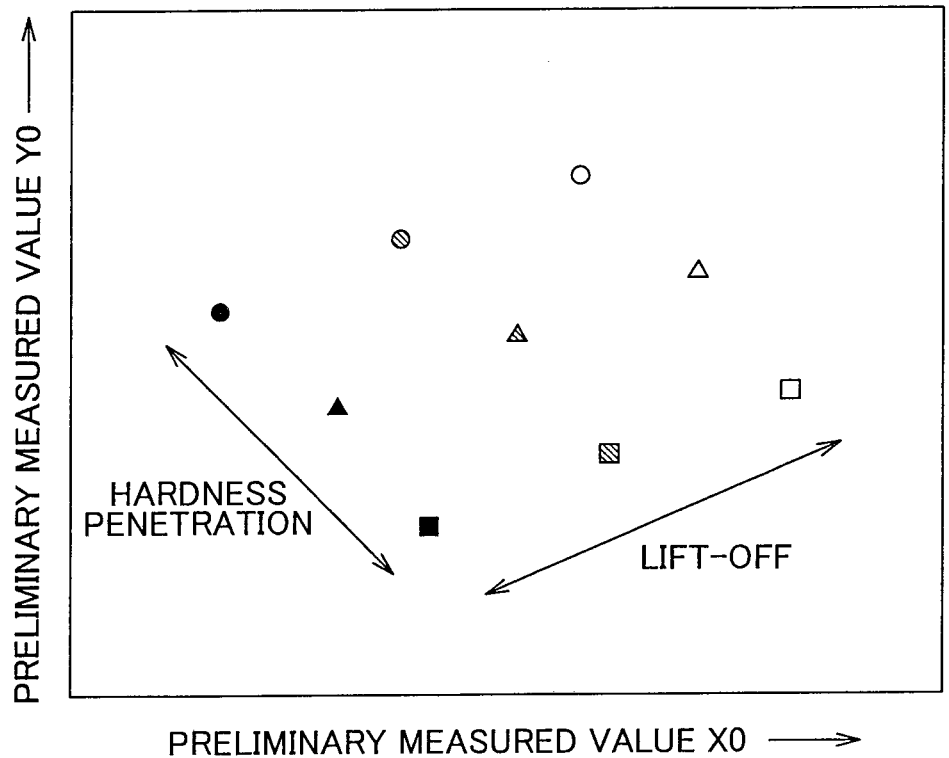
FIG. 6 is a graph that shows preliminary measured values in the eddy current sensor according to the first embodiment.

Next, an eddy current measurement method that uses the eddy current sensor according to the present embodiment to measure the hardness penetration of a measurement object component will be described with reference to FIG. 6 to FIG. 8. The eddy current measurement method according to the present embodiment includes a preliminary measurement step, a preliminary rotation step, a calibration curve generating step, a measurement step, a rotation step and a hardness penetration measurement step. Hereinafter, the steps will be specifically described.

First, in the preliminary measurement step, preliminary measurement object components that have been quenched with known hardness penetrations are prepared one by one for each hardness penetration. In the present embodiment, as shown in the legend in FIG. 6, preliminary measurement object components respectively having hardness penetrations of 1.4 mm, 2.8 mm and 4.2 mm are used. Then, a plurality of lift-off patterns are set at the time of quenching measurement over the preliminary measurement object components, and then detection signals for the respective preliminary measurement object components are detected for each lift-off by the eddy current sensor. In the present embodiment, as shown in the legend in FIG. 6, eddy current measurement is conducted in three large, medium, small lift-off patterns. Furthermore, as shown in FIG. 6, a preliminary measured value X0 that is a measured eddy current value in the X direction and a preliminary measured value Y0 that is a measured eddy current value in the Y direction on the X-Y coordinate plane are calculated from the detection signal for each hardness penetration and each measurement distance.

In this process, a variation in output value due to a variation in the hardness penetration of a preliminary measurement object component and a variation in output value due to a variation in lift-off (measurement distance that the probe coil measures a preliminary measurement object component) are output with different characteristics. Specifically, as shown in FIG. 6, when the hardness penetration increases, the preliminary measured values X0 and Y0 that are output values each correlate with the hardness penetration in an opposite manner. More specifically, when the hardness penetration increases, the preliminary measured value X0 increases and the preliminary measured value Y0 reduces, so the preliminary measured values X0 and Y0 are plotted from the top left to the bottom right on the X-Y coordinate plane. On the other hand, when the lift-off increases, the preliminary measured values X0 and Y0 that are output values each correlate with the lift-off in a similar manner. More specifically, when the lift-off increases, both the preliminary measured values X0 and Y0 reduce, so the preliminary measured values X0 and Y0 are plotted from the top right to the bottom left on the X-Y coordinate plane.

Subsequently, in the preliminary rotation step, the preliminary measured value X0 and the preliminary measured value Y0 that are detected for each hardness penetration and each measurement distance are subjected to phase rotation on the X-Y coordinate plane. Specifically, when the hardness penetration is the same, a phase rotation angle θ is set so that any one of a set of preliminary rotation values X1 and a set of preliminary rotation values Y1 is substantially constant to thereby calculate the preliminary rotation values X1 corresponding to the preliminary measured values X0 and the preliminary rotation values Y1 corresponding to the preliminary measured values Y0. In the present embodiment, as shown in FIG. 7, when the hardness penetration is the same, the phase rotation angle θ is set so that the preliminary rotation values Y1 are substantially constant.

The phase rotation in this step uses the following mathematical expression (1) and mathematical expression (2) to calculate the preliminary rotation values X1 corresponding to the preliminary measured values X0 and the preliminary rotation values Y1 corresponding to the preliminary measured values Y0.

$$X1 = X0 \cos(\pi/180)\theta - Y0 \sin(\pi/180)\theta \quad (1)$$

$$Y1 = X0 \sin(\pi/180)\theta + Y0 \cos(\pi/180)\theta \quad (2)$$

Figure 7:
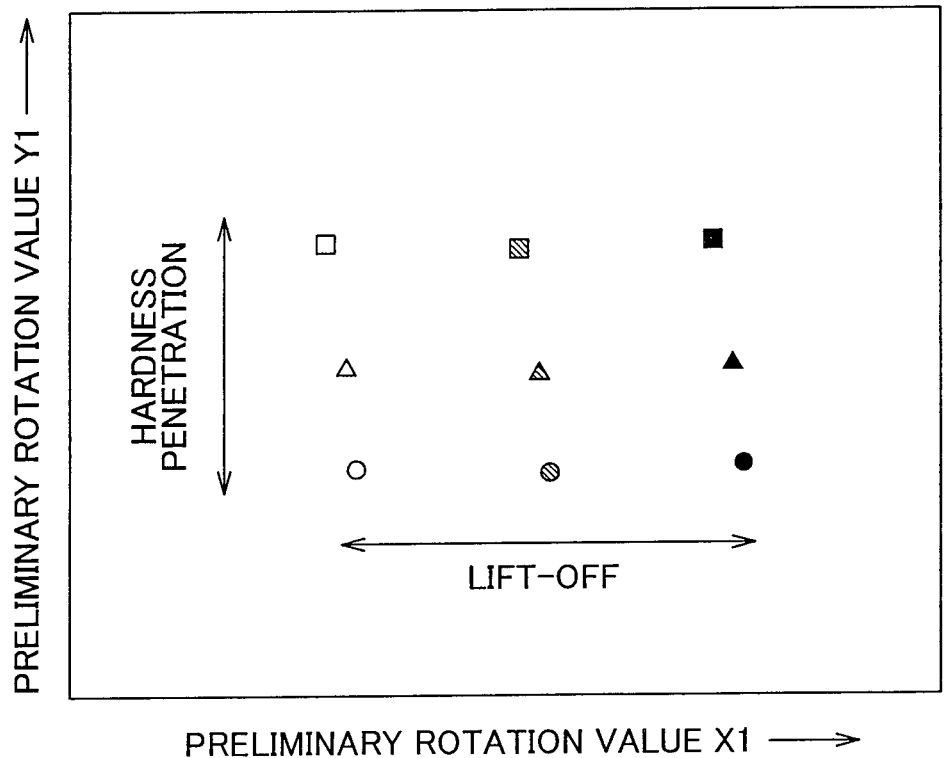
FIG. 7 is a graph that shows preliminary rotation values in the eddy current sensor according to the first embodiment.
Figure 8:
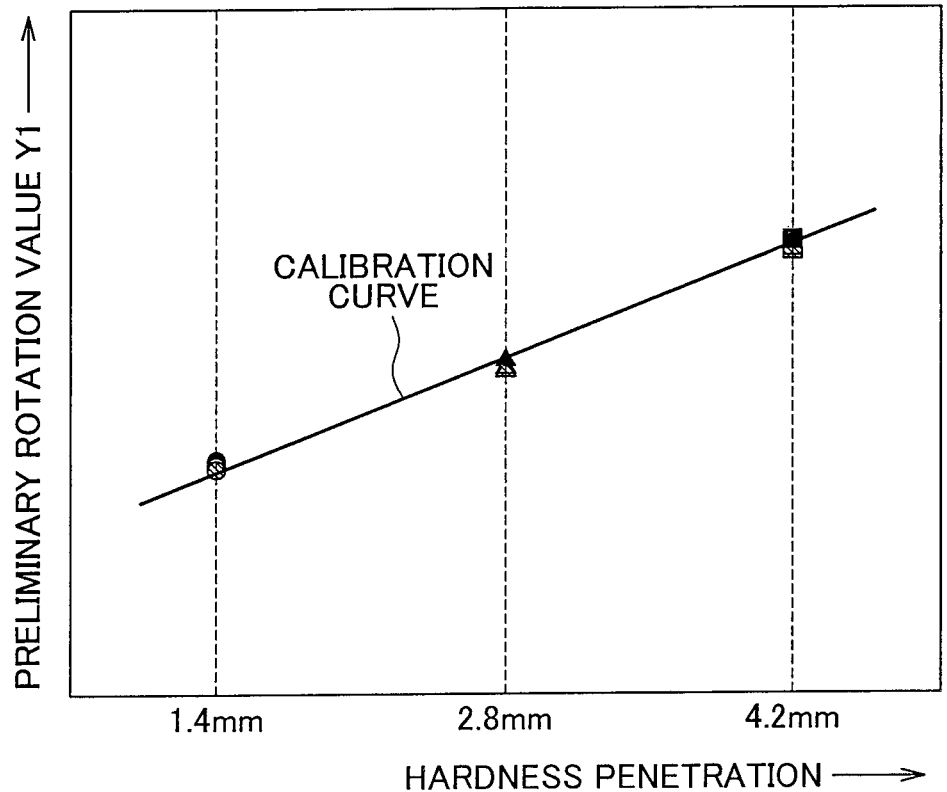
FIG. 8 is a schematic graph that shows a calibration curve in the eddy current sensor according to the first embodiment.

That is, the phase rotation angle θ is set so that, when the preliminary measured values X0 and Y0 and the phase rotation angle θ are substituted into the mathematical expressions (1) and (2), the preliminary rotation values Y1 are substantially constant when the hardness penetrations are the same as shown in FIG. 7.

After that, in the calibration curve generating step, a hardness penetration calibration curve is generated. The hardness penetration calibration curve indicates the correlation between the hardness penetration and the preliminary rotation value Y1 that is made substantially constant in the preliminary rotation step. Specifically, as shown in FIG. 8, a coordinate plane is generated so that the abscissa axis represents 1.4 mm, 2.8 mm and 4.2 mm as known hardness penetrations and the ordinate axis represents preliminary rotation values Y1 corresponding to the respective hardness penetrations. Then, a hardness penetration calibration curve is drawn in a straight line so as to uniformly pass through the plots. Note that, when the phase rotation angle θ is set in the preliminary rotation step so that the preliminary rotation values X1 are substantially constant, the hardness penetration calibration curve that indicates the correlation between the preliminary rotation value X1 and the hardness penetration is generated. In addition, in the present embodiment, the hardness penetration calibration curve is generated in a straight line; however, the hardness penetration calibration curve may be expressed by another function expression, such as a parabola expressed by a quadric.

Then, in the measurement step, a detection signal for a measurement object component is detected by the eddy current sensor as described above, a measured eddy current value x0 in the X direction and a measured eddy current values y0 in the Y direction on the X-Y coordinate plane are calculated from the detection signal.

Subsequently, in the rotation step, the measured eddy current value x0 and the measured eddy current value y0 are subjected to phase rotation on the X-Y coordinate plane with the same phase rotation angle θ as the phase rotation in the preliminary rotation step to thereby calculate a measured rotation value x1 corresponding to the measured eddy current value x0 and a measured rotation value y1 corresponding to the measured eddy current value y0.

Then, in the hardness penetration measurement step, the hardness penetration of the portion of the measurement object component, facing the detection coil 61, is measured from the correlation between the measured rotation value y1 and the hardness penetration calibration curve. Specifically, the measured rotation value y1 is taken on the ordinate axis shown in FIG. 8, and the hardness penetration of a corresponding point on the hardness penetration calibration curve is measured as the hardness penetration of the measurement object component. Note that, when the hardness penetration calibration curve that indicates the correlation between the preliminary rotation value X1 and the hardness penetration is generated, the hardness penetration of the portion of the measurement object component, facing the detection coil 61, is measured from the correlation between the measured rotation value x1 and the hardness penetration calibration curve.

The thus configured eddy current measurement method according to the present embodiment may be used to conduct hardness penetration measurement test with high detection accuracy even when an induction quenched component of which the outside diameter varies by a large amount is inspected. That is, eddy current measurement is carried out in such a manner that the eddy current sensor is brought into proximity with a measurement object component, so the eddy current measurement is less influenced by a variation in the outside diameter of the measurement object component.

The eddy current measurement method according to the present embodiment eliminates the influence of lift-off in measuring the hardness penetration to thereby make it possible to improve measurement accuracy. Specifically, as described above, a variation in output value due to a variation in the hardness penetration of a measurement object component and a variation in output value due to a variation in lift-off are output with different characteristics. Therefore, the preliminary measured values X0 and the preliminary measured values Y0 are subjected to phase rotation on the X-Y coordinate plane to thereby make it possible to obtain the preliminary rotation values Y1 that are not influenced by lift-off and that vary only depending on the hardness penetration. Then, the hardness penetration is measured using the calibration curve based on the correlation between the preliminary rotation value Y1 and the hardness penetration. By so doing, it is possible to eliminate the influence of lift-off in measuring the hardness penetration, so it is possible to improve measurement accuracy.

Next, an eddy current sensor according to a second embodiment of the invention will be described with reference to FIG. 9A. Note that the detailed description of components of the eddy current sensors according to the present and following embodiments common to the above described embodiment is omitted. In addition, for the eddy current sensors described in the present and following embodiments, a case that accommodates an exciting portion and a detecting portion is not shown in the drawing.

Figure 9A:
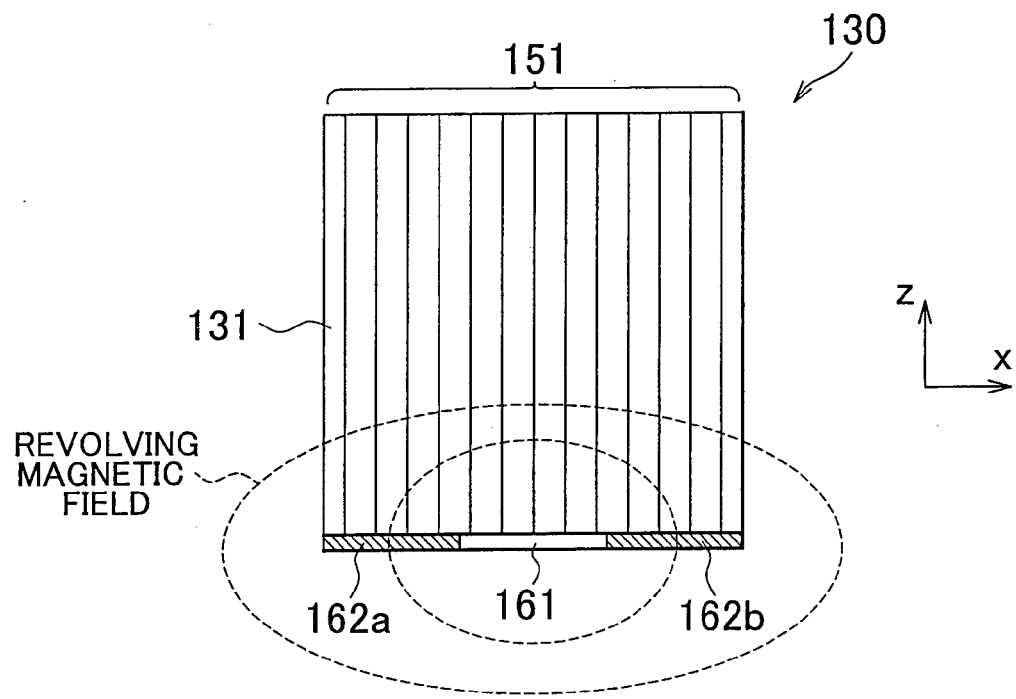
FIG. 9A is a side view that shows the configuration of an eddy current sensor according to a second embodiment.

As shown in FIG. 9A, the eddy current sensor according to the present embodiment includes a probe 130 as in the case of the first embodiment. The probe 130 includes an exciting portion and a detecting portion. The exciting portion is formed so that a first excitation coil 151 and a second excitation coil (not shown) are wound around a substantially cubular non-magnetic bobbin 131. That is, the first excitation coil 151 and the second excitation coil are arranged so as to intersect at right angles with each other on the top surface and bottom surface of the non-magnetic bobbin 131. The detecting portion includes the detection coil 161 that is arranged at the lower one of two intersecting portions of the first excitation coil 151 and the second excitation coil.

In the present embodiment, the detecting portion includes two quenching determination coils 162a and 162b that are arranged adjacent to the detection coil 161 on both sides in the x-axis direction. The detection coil 161 is arranged at a substantially center portion of the first excitation coil 151 in the x-axis direction, and the quenching determination coils 162a and 162b are respectively arranged at both end portions of the first excitation coil 151 in the x-axis direction. In the present embodiment, a thin-film planar coil is used as the quenching determination coils 162a and 162b; instead, another coil, such as a pancake coil, may also be used. In addition, it is also applicable that the single quenching determination coil 162a is arranged adjacent to the detection coil 161 only on one side of the detection coil 162a. Both ends (both terminals) of each of the quenching determination coils 162a and 162b are connected to a measurement device of a computing unit (not shown). That is, the quenching determination coils 162a and 162b detect detection signals, generated by eddy currents, from a measurement object component to which the alternating-current excitation signal is applied.

When the thus configured eddy current sensor is used to measure the hardness penetration of a measurement object component, alternating-current voltage is applied to each of the first excitation coil 151 and the second excitation coil by the alternating-current power supply in a state where the probe 130 is arranged in proximity to the measurement object component in position such that the detection coil 161 and the quenching determination coils 162a and 162b face the measured portion of the measurement object component. At the moment at which current flows through the first excitation coil 151, a revolving magnetic field is generated around the first excitation coil 151 in accordance with the corkscrew rule. At this time, as shown in FIG. 9A, a horizontal magnetic field in the x-axis direction is strongly generated around the center portion of the probe 130, and a vertical magnetic field in the z-axis direction is strongly generated around both end portions of the probe 130.

When the measurement object component has been quenched, the magnetic permeability significantly varies. Here, the vertical magnetic field is more easily influenced by a variation in magnetic permeability than the horizontal magnetic field, so, when it is determined whether the measurement object component is quenched or not quenched, it is more effective and reliable when a variation in magnetic permeability owing to the vertical magnetic field is read (see FIG. 10 to FIG. 12).

In the present embodiment, as described above, among the magnetic fields generated by the first excitation coil 151, the vertical magnetic field is used in eddy current measurement for determining whether the measurement object component is quenched or not quenched. That is, the vertical magnetic field is generated at portions of the measurement object component, facing the quenching determination coils 162a and 162b. Then, electromagnetic induction is caused by the vertical magnetic fields, and eddy currents are generated by the electromagnetic induction in the measurement object component that is a magnetic material. Furthermore, with the generation of eddy currents at the surface of the measurement object component, magnetic fluxes pass through the quenching determination coils 162a and 162b to cause the quenching determination coils 162a and 162b to generate induced voltages. Then, the induced voltages are measured as detection signals by the quenching determination coils 162a and 162b. Then, the computing unit calculates the detection signals of the quenching determination coils 162a and 162b as measured eddy current values, and determines whether the portions of the measurement object component, respectively facing the quenching determination coils 162a and 162b, are quenched or not quenched on the basis of the measured eddy current values.

In the present embodiment, as described above, the vertical magnetic field that is easily influenced by a variation in magnetic permeability is used in eddy current measurement, so it is possible to effectively and reliably determine whether the measurement object component is quenched or not quenched.

Next, an eddy current measurement method that uses the eddy current sensor according to the present embodiment to measure the hardness penetration of a measurement object component will be described with reference to FIG. 10 to FIG. 12. Note that the detailed description of portions of the eddy current measurement method described in the present and following embodiments, common to the above described embodiments, is omitted.

The eddy current measurement method according to the present embodiment includes a preliminary quenching measurement step, a reference calculating step, a preliminary measurement step, a preliminary rotation step, a calibration curve generating step, a quenching measurement step, a quenching determination step, a measurement step, a rotation step and a hardness penetration measurement step. Hereinafter, the steps will be specifically described.

First, in the preliminary quenching measurement step, a plurality of preliminary quenching measurement object components that are known to be quenched or not quenched are prepared. In the present embodiment, as shown in the legend in FIG. 10, preliminary, quenching measurement object components respectively having hardness penetrations of 1.0 mm, 2.5 mm and 4.0 mm and three non-quenched preliminary quenching measurement object components are used. Then, the quenching determination coils 162a and 162b of the eddy current sensor are used to detect detection signals for each of the preliminary quenching measurement object components, and then calculate the detection signals as preliminary quenching measured values.

Figure 10:
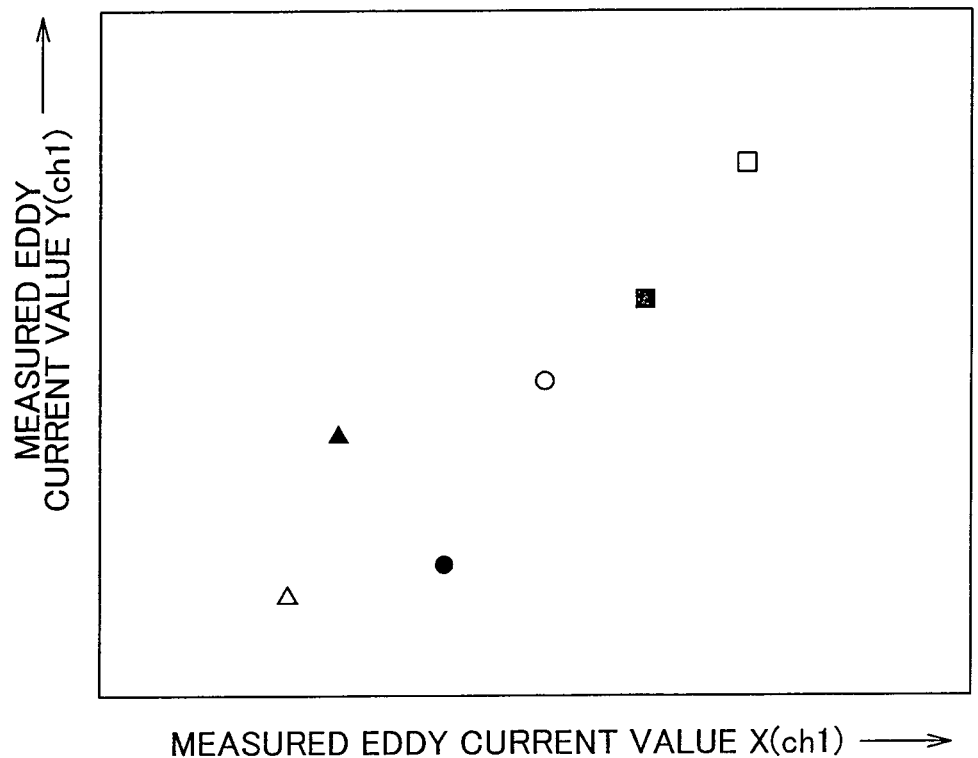
FIG. 10 is a graph that shows measured eddy current values detected by a detection coil in the eddy current sensor according to the second embodiment.
Figure 11:
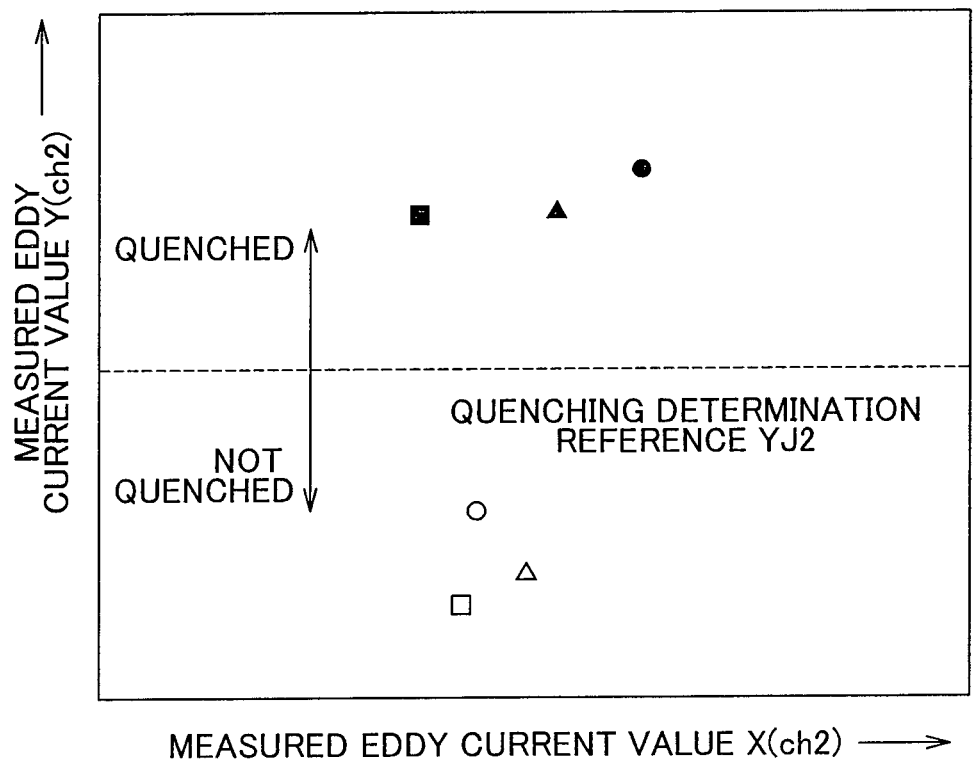
FIG. 11 is a graph that shows measured eddy current values detected by a first quenching determination coil in the eddy current sensor according to the second embodiment.
Figure 12:
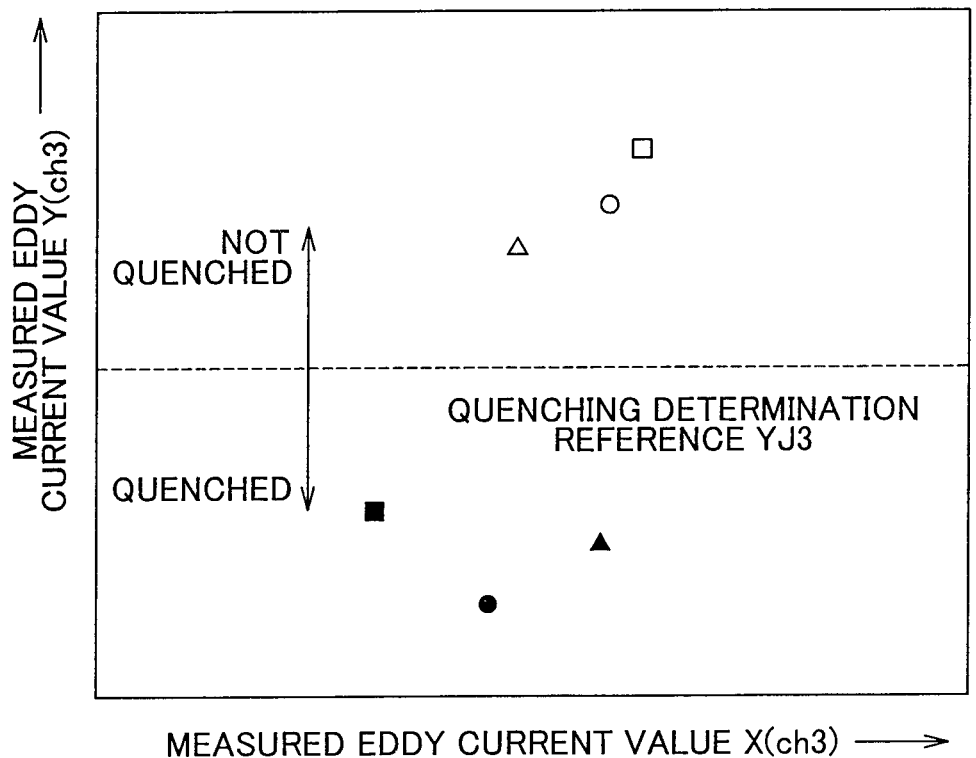
FIG. 12 is a graph that shows measured eddy current values detected by a second quenching determination coil in the eddy current sensor according to the second embodiment.

FIG. 10 to FIG. 12 each show preliminary quenching measured values that are measured eddy current values that are respectively detected by the detection coil 161 and the quenching determination coils 162a and 162b. The measured eddy current values detected by the respective coils are denoted as ch1 to ch3. As shown in FIG. 10, the measured eddy current values (ch1) detected by the detection coil 161 using the horizontal magnetic field for eddy current measurement have no difference between the quenched preliminary quenching measurement object components and the non-quenched preliminary quenching measurement object components, so it is difficult to determine whether the preliminary quenching measurement component is quenched or not quenched. On the other hand, as shown in FIG. 11 and FIG. 12, the measured eddy current values Y (ch2 and ch3) detected by the quenching determination coils 162a and 162b using the vertical magnetic field for eddy current measurement have significant difference between the quenched preliminary quenching measurement object components and the non-quenched preliminary quenching measurement object components, it is possible to determine whether the preliminary quenching measurement component is quenched or not quenched.

Subsequently, in the reference calculating step, a quenching determination reference that indicates preliminary quenching measured values is calculated for each of the quenching determination coils 162a and 162b. That is, as shown in FIG. 11 and FIG. 12, quenching determination references YJ2 and YJ3, each of which indicates the boundary as to whether the preliminary quenching measurement object component is quenched or not quenched, are calculated on the basis of the measured eddy current values Y (ch2 and ch3) resulting from whether the preliminary quenching measurement object component is quenched or not. In this case, the quenching determination references YJ2 and YJ3 are desirably set so as to be able to reliably separate the measured eddy current values Y in the case of the quenched preliminary quenching measurement object component and the measured eddy current values Y in the case of the non-quenched preliminary quenching measurement object component from each other as much as possible.

Subsequently, as in the case of the above embodiment, the preliminary measurement step, the preliminary rotation step and the calibration curve generating step are executed.

After that, in the quenching measurement step, the quenching determination coils 162a and 162b of the eddy current sensor are used to detect detection signals for a measurement object component, and calculates the detection signals as quenching measured eddy current values for the respective quenching determination coils 162a and 162b.

Then, in the quenching determination step, the quenching measured eddy current values, calculated on the basis of the corresponding quenching determination coils 162a and 162b, are respectively compared with the quenching determination references YJ2 and YJ3 to thereby determine whether the portions of the measurement object component, respectively facing the quenching determination coils 162a and 162b, are quenched or not quenched. Specifically, it is determined whether the portions of the measurement object component, respectively facing the quenching determination coils 162a and 162b, are quenched or not quenched on the basis of whether the quenching measured eddy current values that are the measured eddy current values Y detected by the quenching determination coils 162a and 162b respectively exceed the quenching determination references YJ2 and YJ3.

Subsequently, in the measurement step, a detection signal for the measurement object component that is determined in the quenching determination step that all the quenching determination portions (portions respectively facing the quenching determination coils 162a and 162b) are quenched is detected by the eddy current sensor, and then the detection signal is used to calculate a measured eddy current value x0 in the X direction and a measured eddy current value y0 in the Y direction on the X-Y coordinate plane.

After that, as in the case of the first embodiment, the rotation step and the hardness penetration measurement step are executed to measure the hardness penetrations of the portion of the measurement object component, facing the detection coil 161.

In the present embodiment, as described above, the vertical magnetic field that is easily influenced by a variation in magnetic permeability is used in eddy current measurement for determining whether the measurement object component is quenched or not quenched, so it is possible to effectively and reliably determine whether the measurement object component is quenched or not quenched. By so doing, it is possible to improve the efficiency of eddy current measurement in such a manner that it is determined whether a measurement object component is quenched or not quenched before measuring the hardness penetration and then the hardness penetration of a measurement object component that is not sufficiently quenched is not measured.

Figure 9B:
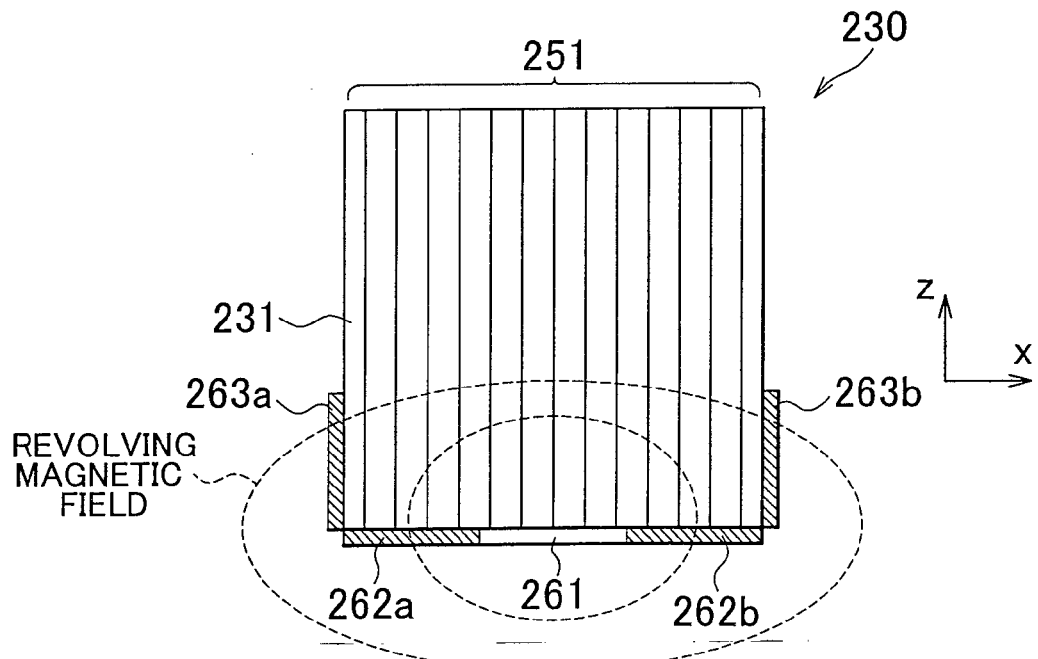
FIG. 9B is a side view that shows the configuration of an eddy current sensor according to a third embodiment.

Next, an eddy current sensor according to a third embodiment of the invention will be described with reference to FIG. 9B. As shown in FIG. 9B, the eddy current sensor according to the present embodiment includes a probe 230 as in the case of the first embodiment. The probe 230 includes an exciting portion and a detecting portion. The exciting portion is formed so that a first excitation coil 251 and a second excitation coil (not shown) are wound around a substantially cubular non-magnetic bobbin 231. That is, the first excitation coil 251 and the second excitation coil are arranged so as to intersect at right angles with each other on the top surface and bottom surface of the non-magnetic bobbin 231. The detecting portion includes a detection coil 261 and two quenching determination coils 262a and 262b. The detection coil 261 is arranged at the lower one of two intersecting portions of the first excitation coil 251 and the second excitation coil. The two quenching determination coils 262a and 262b are arranged adjacent to the detection coil 261 on both sides in the x-axis direction.

In the present embodiment, the detecting portion includes two perpendicular quenching determination coils 263a and 263b on the opposite sides of the quenching determination coils 262a and 262b with respect to the detection coil 261. The two perpendicular quenching determination coils 263a and 263b are arranged perpendicularly to the quenching determination coils 262a and 262b. The detection coil 261 is arranged at a substantially center portion of the first excitation coil 251 in the x-axis direction. The quenching determination coils 262a and 262b are respectively arranged at both end portions of the first excitation coil 251 in the x-axis direction. The perpendicular quenching determination coils 263a and 263b are respectively arranged at both end portions of the first excitation coil 251 in the x-axis direction. In addition, the detection coil 261 and the quenching determination coils 262a and 262b are respectively arranged at a substantially center portion and both end portions of the bottom surface of the non-magnetic bobbin 231 in the x-axis direction, and the perpendicular quenching determination coils 263a and 263b are arranged at lower end portions of both side surfaces adjacent to both ends of the bottom surface of the non-magnetic bobbin 231 in the x-axis direction. In the present embodiment, a thin-film planar coil is used as the perpendicular quenching determination coils 263a and 263b; instead, another coil, such as a pancake coil, may also be used. In addition, it is also applicable that the single perpendicular quenching determination coil 263a is arranged adjacent to any one of the quenching determination coils 262a and 262b. Both ends (both terminals) of each of the perpendicular quenching determination coils 263a and 263b are connected to a measurement device of a computing unit (not shown). That is, the perpendicular quenching determination coils 263a and 263b detect detection signals, generated by eddy currents, from a measurement object component to which the alternating-current excitation signal is applied.

Figure 13A:
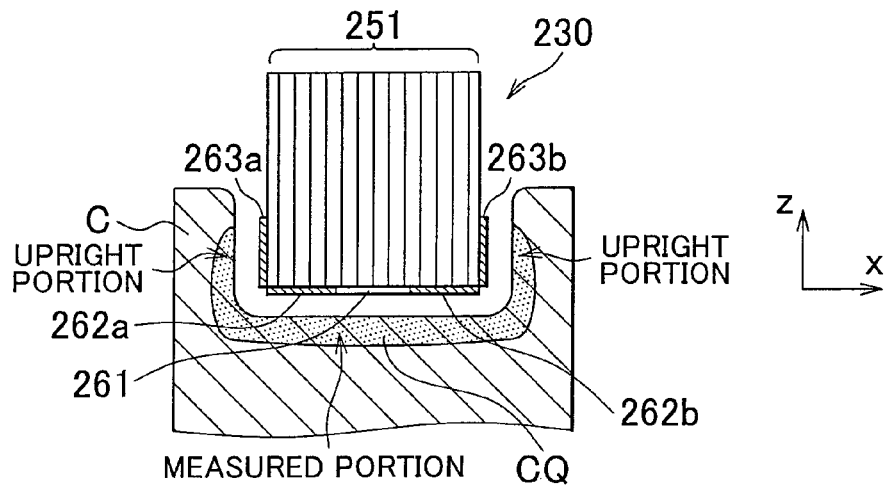
FIG. 13A, FIG. 13B and FIG. 13C are side views that respectively show measuring states of the eddy current sensor according to the third embodiment.
Figure 13B:
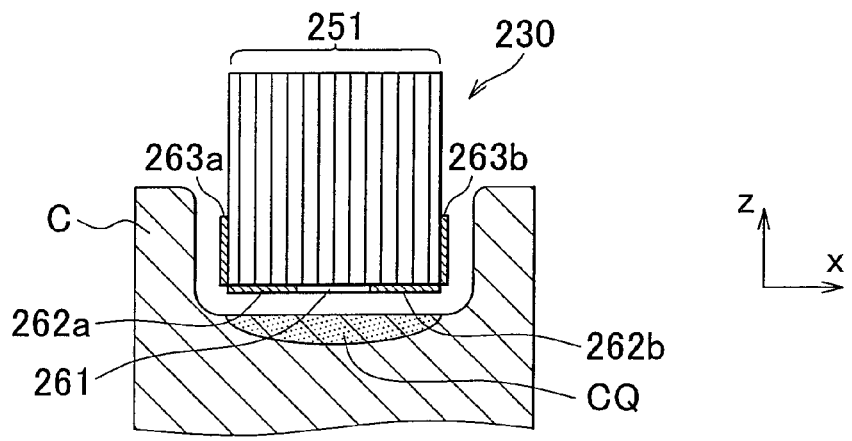
Figure 13C:
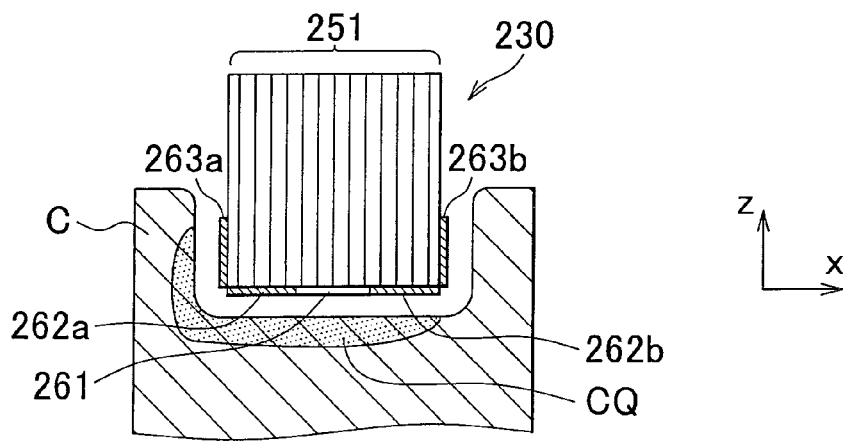

It is assumed that the measurement object component in the present embodiment is a crankshaft C (a pin portion or journal portion of the crankshaft C) that has a measured portion and upright portions located on both ends of the measured portion so as to be perpendicular to the measured portion as shown in FIG. 13A to FIG. 13C. When the thus configured eddy current sensor is used to measure the hardness penetration of the crankshaft C, the probe 230 is arranged in proximity to the crankshaft C in position such that the detection coil 261 and the quenching determination coils 262a and 262b face the measured portion of the crankshaft C and the perpendicular quenching determination coils 263a and 263b face the upright portions perpendicular to the measured portion of the crankshaft C, as shown in FIG. 13A to FIG. 13C. Then, in this state, alternating-current is applied to each of the first excitation coil 251 and the second excitation coil to thereby generate a magnetic field in the x-axis direction at both end portions of the measured portion of the crankshaft C and the upright portions of the crankshaft C, as shown in FIG. 9B. That is, the vertical magnetic field is generated at portions facing the quenching determination coils 262a and 262b and portions facing the perpendicular quenching determination coils 263a and 263b in the crankshaft C.

Furthermore, eddy currents are generated by the vertical magnetic fields, and induced voltages generated by the eddy currents are detected by the quenching determination coils 262a and 262b and the perpendicular quenching determination coils 263a and 263b as detection signals. Then, the computing unit calculates the detection signals detected by the quenching determination coils 262a and 262b and the perpendicular quenching determination coils 263a and 263b as measured eddy current values to thereby determine whether the portions of the crankshaft C, respectively facing the quenching determination coils 262a and 262b and the perpendicular quenching determination coils 263a and 263b, are quenched or not quenched on the basis of the measured eddy current values.

FIG. 13A shows the case where a quenched portion CQ extends over the measured portion and upright portions of the crankshaft C. In this case, the measured eddy current values detected by all the quenching determination coils 262a and 262b and the perpendicular quenching determination coils 263a and 263b indicate to determine that the measured portion and the upright portions are quenched.

FIG. 13B shows the case where a quenched portion CQ extends over only the measured portion of the crankshaft C. In this case, the measured eddy current values detected by the quenching determination coils 262a and 262h indicate to determine that the measured portion is quenched; however, the measured eddy current values detected by the perpendicular quenching determination coils 263a and 263b indicate to determine that the upright portions are not quenched.

FIG. 13C shows the case where a quenched portion CQ extends over the measured portion and only one-side upright portion (adjacent to the perpendicular quenching determination coil 263a) of the crankshaft C. In this case, the measured eddy current value detected by the quenching determination coils 262a and 262b and the perpendicular quenching determination coil 263a indicate to determine that the measured portion and one of the upright portions are quenched; however, the measured eddy current value detected by the perpendicular quenching determination coil 263b indicates to determine that the other one of the upright portions is not quenched.

In the present embodiment, as described above, even when the crankshaft C has a shape having the upright portions perpendicular to the measured portion, the vertical magnetic fields generated at the portions facing the perpendicular quenching determination coils 263a and 263b are used for eddy current measurement, so it is possible to determine whether the upright portions are quenched or not quenched.

Next, an eddy current measurement method that uses the eddy current sensor according to the present embodiment to measure the hardness penetration of the crankshaft C that is the measurement object component will be described.

The eddy current measurement method according to the present embodiment includes a preliminary quenching measurement step, a reference calculating step, a preliminary measurement step, a preliminary rotation step, a calibration curve generating step, a quenching measurement step, a quenching determination step, a measurement step, a rotation step and a hardness penetration measurement step. Hereinafter, the steps will be specifically described.

First, in the preliminary quenching measurement step, a plurality of crankshafts C that are preliminary quenching measurement object components, each of which has a measured portion and upright portions perpendicular to the measured portion and is known to be quenched or not quenched, are prepared. Then, detection signals for the measured portion and upright portions of each of the quenched crankshafts C are respectively detected by the quenching determination coils 262a and 262b and perpendicular quenching determination coils 263a and 263b of the eddy current sensor, and then the detection signals are respectively calculated as preliminary quenching measured values for the quenching determination coils 262a and 262b and the perpendicular quenching determination coils 263a and 263b.

Subsequently, in the reference calculating step, a quenching determination reference that indicates preliminary quenching measured values is calculated for each of the quenching determination coils 262a and 262b and the perpendicular quenching determination coils 263a and 263b.

After that, as in the case of the above embodiment, the preliminary measurement step, the preliminary rotation step, the calibration curve generating step and the quenching measurement step are executed.

Then, in the perpendicular quenching measurement step, detection signals for the upright portions of the crankshaft C are respectively detected by the perpendicular quenching determination coils 263a and 263b of the eddy current sensor, and then the detection signals are respectively calculated as perpendicular quenching measured eddy current values for the perpendicular quenching determination coils 263a and 263b.

Subsequently, in the quenching determination step, the quenching measured eddy current values and perpendicular quenching measured eddy current values and the quenching determination references, which are calculated on the basis of the corresponding quenching determination coils 262a and 262b and perpendicular quenching determination coils 263a and 263b, are compared to determine whether the measured portion and upright portions of the crankshaft C are quenched or not quenched.

After that, in the measurement step, for the crankshaft C that is determined in the quenching determination step that all the measured portion and upright portions are quenched as shown in FIG. 13A, detection signals are detected by the eddy current sensor, and then measured eddy current values x0 in the X direction and measured eddy current values y0 in the Y direction on the X-Y coordinate plane are calculated from the detection signals.

Then, as in the case of the first embodiment, the rotation step and the hardness penetration measurement step are executed to measure the hardness penetration of the portion of the crankshaft C, facing the detection coil 261.

In the present embodiment, as described above, even when the crankshaft C has a shape having the upright portions perpendicular to the measured portion, the vertical magnetic fields generated at the portions facing the perpendicular quenching determination coils 263a and 263b are used for eddy current measurement, so it is possible to determine whether the upright portions are quenched or not quenched. By so doing, it is possible to improve the efficiency of eddy current measurement in such a manner that it is determined whether a crankshaft C is quenched or not quenched before measuring the hardness penetration and then the hardness penetration of a crankshaft C that is not sufficiently quenched is not measured.

Figure 14A:
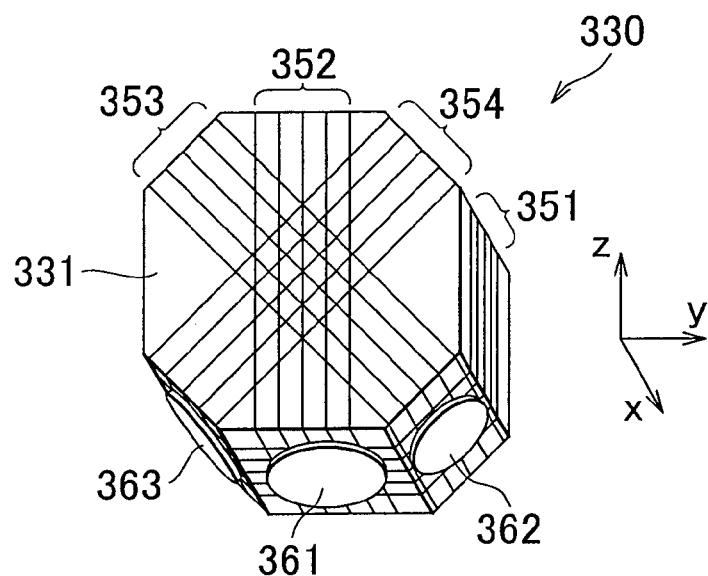
FIG. 14A is a schematic view that shows the configuration of an eddy current sensor according to a fourth embodiment.
Figure 14B:
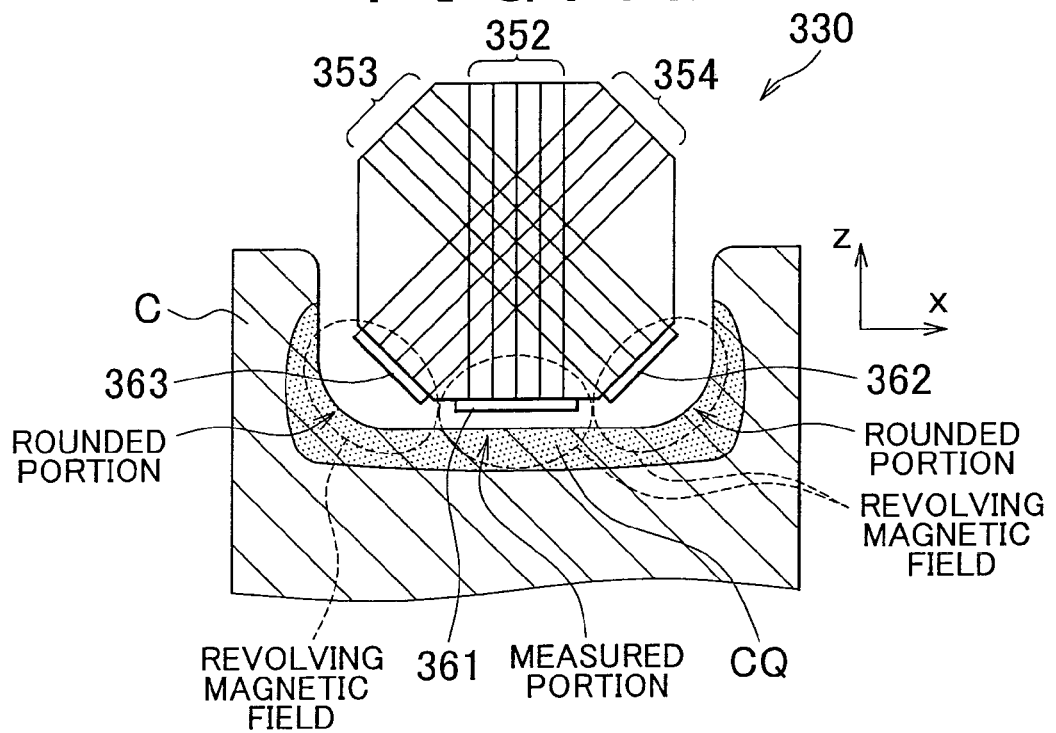
FIG. 14B is a side view that shows a measuring state of the eddy current sensor according to the fourth embodiment.

Next, an eddy current sensor according to a fourth embodiment of the invention will be described with reference to FIG. 14A and FIG. 14B. As shown in FIG. 14A and FIG. 14B, the eddy current sensor according to the present embodiment includes a probe 330 as in the case of the first embodiment. The probe 330 includes an exciting portion and a detecting portion, and is formed in an octagonal prism shape of which the axis is oriented in the x-axis direction. Note that the shape of the probe 330 is not limited to an octagonal prism shape.

The exciting portion includes a first excitation coil 351, a second excitation coil 352, a third excitation coil 353 and a fourth excitation coil 354 each of which is wound around the octagonal prism-shaped non-magnetic bobbin 331. The first excitation coil 351 is wound around the non-magnetic bobbin 331 so that the center axis direction is oriented in the x-axis direction. The second excitation coil 352 is wound around the non-magnetic bobbin 331 to intersect with the first excitation coil 351 so that the center axis direction is oriented in the y-axis direction. The third excitation coil 353 and the fourth excitation coil 354 are wound around the non-magnetic bobbin 331 to intersect with the first excitation coil 351 so that the center axis directions are oriented in directions perpendicular to the x-axis direction and inclined equally with respect to the y-axis direction.

Both ends (both terminals) of each excitation coil are connected to an alternating-current power supply (not shown). That is, each excitation coil is an excitation coil for applying a predetermined alternating-current excitation signal to the crankshaft C that is a measurement object component.

The detecting portion includes a first detection coil 361, a second detection coil 362 and a third detection coil 363. The first detection coil 361 is arranged at one of two intersecting portions of the first excitation coil 351 and the second excitation coil 352. The second detection coil 362 is arranged at one of two intersecting portions of the first excitation coil 351 and the third excitation coil 353, adjacent to the first detection coil 361. The third detection coil 363 is arranged at one of two intersecting portions of the first excitation coil 351 and the fourth excitation coil 354, adjacent to the first detection coil 361.

Both ends (both terminals) of each detection coil are connected to a measurement device of a computing unit (not shown). That is, the detection coils respectively detect detection signals, generated by eddy currents, from the crankshaft C to which the alternating-current excitation signal is applied.

When the thus configured eddy current sensor is used to measure the hardness penetration of a quenched portion CQ in a portion of the crankshaft C, having a measured portion and upright portions located on both ends of the measured portion and perpendicular to the measured portion (a pin portion or journal portion of the crankshaft C), the probe 330 is arranged in proximity to the crankshaft C in position such that the first detection coil 361 faces the measured portion of the crankshaft C and the second detection coil 362 and the third detection coil 363 face the boundary portions between the measured portion and the upright portions, as shown in FIG. 14B. That is, the second detection coil 362 and the third detection coil 363 face rounded portions formed at both ends of the measured portion of the crankshaft C. In this state, alternating-current voltage is applied to each of the first excitation coil 351, the second excitation coil 352, the third excitation coil 353 and the fourth excitation coil 354 as an alternating-current excitation signal. Then, magnetic fields are generated in the crankshaft C.

At this time, revolving magnetic fields shown in FIG. 14B are respectively generated by the second excitation coil 352, the third excitation coil 353 and the fourth excitation coil 354 around the first detection coil 361, the second detection coil 362 and the third detection coil 363. That is, horizontal magnetic fields that are horizontal to the respective detection coils are generated by the second excitation coil 352, the third excitation coil 353 and the fourth excitation coil 354. Then, electromagnetic induction is caused by the horizontal magnetic fields, and eddy currents are generated in the crankshaft C that is a magnetic material through the electromagnetic induction. Furthermore, with the generation of eddy currents at the surface of the crankshaft C, induced voltages generated by the eddy currents are detected by the first detection coil 361, the second detection coil 362 and the third detection coil 363 as detection signals, and the computing unit calculates the detection signals as measured eddy current values to thereby measure the hardness penetration of the portions of the crankshaft C, respectively facing the first detection coil 361, the second detection coil 362 and the third detection coil 363, on the basis of the measured eddy current values.

Next, an eddy current measurement method that uses the eddy current sensor according to the present embodiment to measure the hardness penetration of the crankshaft C that is the measurement object component will be described with reference to FIG. 14B. The eddy current measurement method according to the present embodiment includes a preliminary measurement step, a preliminary rotation step, a calibration curve generating step, a first measurement step, a second measurement step, a third measurement step, a rotation step, a first hardness penetration measurement step, a second hardness penetration measurement step and a third hardness penetration measurement step. Hereinafter, the steps will be specifically described.

First, as in the case of the first embodiment, the preliminary measurement step, the preliminary rotation step and the calibration curve generating step are executed.

Subsequently, in the first measurement step, a detection signal for the crankshaft C is detected by the first detection coil 361 of the eddy current sensor, and then a first measured eddy current value x01 in the X direction and a first measured eddy current value y01 in the Y direction on the X-Y coordinate plane are calculated from the detection signal. After that, similarly in the second measurement step and the third measurement step, detection signals for the crankshaft C are respectively detected by the second detection coil 362 and the third detection coil 363, and then a second measured eddy current value x02 in the X direction, a second measured eddy current value y02 in the Y direction, a third measured eddy current value x03 in the X direction and a third measured eddy current value y03 in the Y direction on the X-Y coordinate plane are calculated from the detection signals.

Then, in the rotation step, the first measured eddy current value x01, the first measured eddy current value y01, the second measured eddy current value x02, the second measured eddy current value y02, the third measured eddy current value x03 and the third measured eddy current value y03 are subjected to phase rotation at the same phase rotation angle as the phase rotation in the preliminary rotation step. Then, a first measured rotation value x11, a first measured rotation value y11, a second measured rotation value x12, a second measured rotation value y12, a third measured rotation value x13 and a third measured rotation value y13 corresponding to the respective measured eddy current values are calculated.

Subsequently, in the first hardness penetration measurement step, the hardness penetration of the portion of the crankshaft C, facing the first detection coil 361, is measured from the correlation between the hardness penetration calibration curve and any one of the first measured rotation value x11 and the first measured rotation value y11. After that, similarly in the second hardness penetration measurement step, the hardness penetration of the portion of the crankshaft C, facing the second detection coil 362, is measured from the correlation between the hardness penetration calibration curve and any one of the second measured rotation value x12 and the second measured rotation value y12. Furthermore, similarly in the third hardness penetration measurement step, the hardness penetration of the portion of the crankshaft C, facing the third detection coil 363, is measured from the correlation between the hardness penetration calibration curve and any one of the third measured rotation value x13 and the third measured rotation value y13.

In the present embodiment, as described above, the horizontal magnetic field of which the attenuation of the magnetic field strength due to lift-off is small is used for eddy current measurement, so the hardness penetration measurement test is less influenced by lift-off. Furthermore, the third excitation coil 353 and the fourth excitation coil 354 are also wound around portions facing the rounded portions of the crankshaft C, and the second detection coil 362 and the third detection coil 363 are arranged. By so doing, it is possible to measure the hardness penetrations of the rounded portions using the horizontal magnetic fields.

Figure 15A:
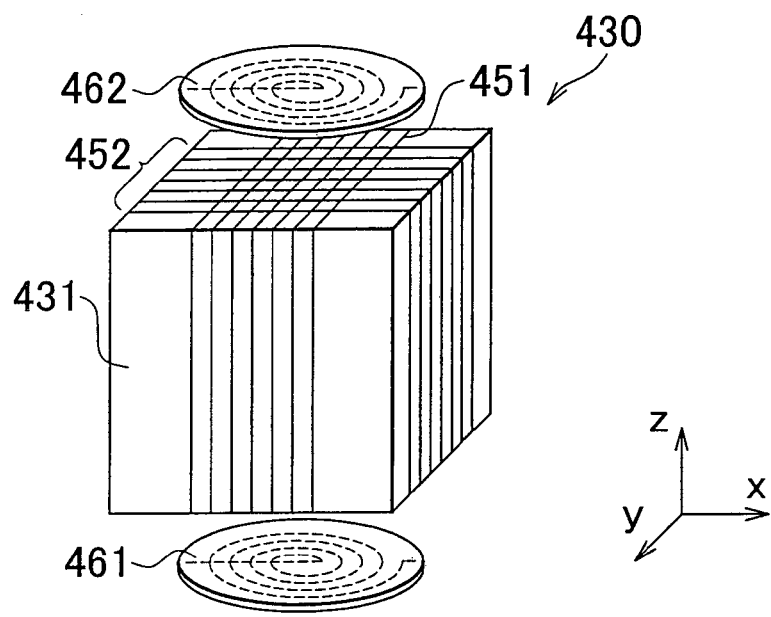
FIG. 15A is a schematic view that shows the configuration of an eddy current sensor according to a fifth embodiment.

Next, an eddy current sensor according to a fifth embodiment of the invention will be described with reference to FIG. 15A and FIG. 15B. As shown in FIG. 15A, the eddy current sensor according to the present embodiment includes a probe 430 as in the case of the first embodiment. The probe 430 includes an exciting portion and a detecting portion. The exciting portion is formed so that a first excitation coil 451 and a second excitation coil 452 are wounded around a substantially cubular non-magnetic bobbin 431. That is, the first excitation coil 451 and the second excitation coil 452 are arranged so as to intersect at right angles with each other on the top surface and bottom surface of the non-magnetic bobbin 431. The detecting portion includes detection coils 461 and 462 that are respectively arranged at both intersecting portions of the first excitation coil 451 and the second excitation coil 452.

Figure 15B:
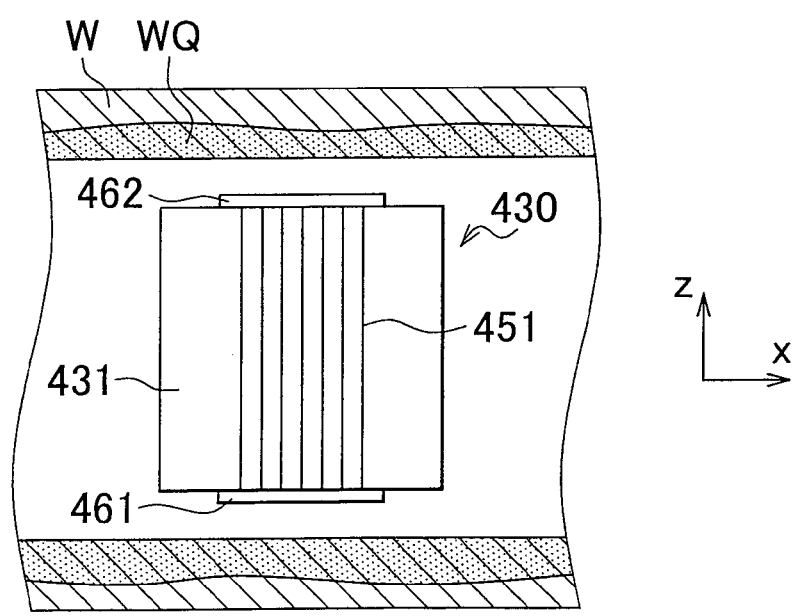
FIG. 15B is a side view that shows a measuring state of the eddy current sensor according to the fifth embodiment.
Figure 16:
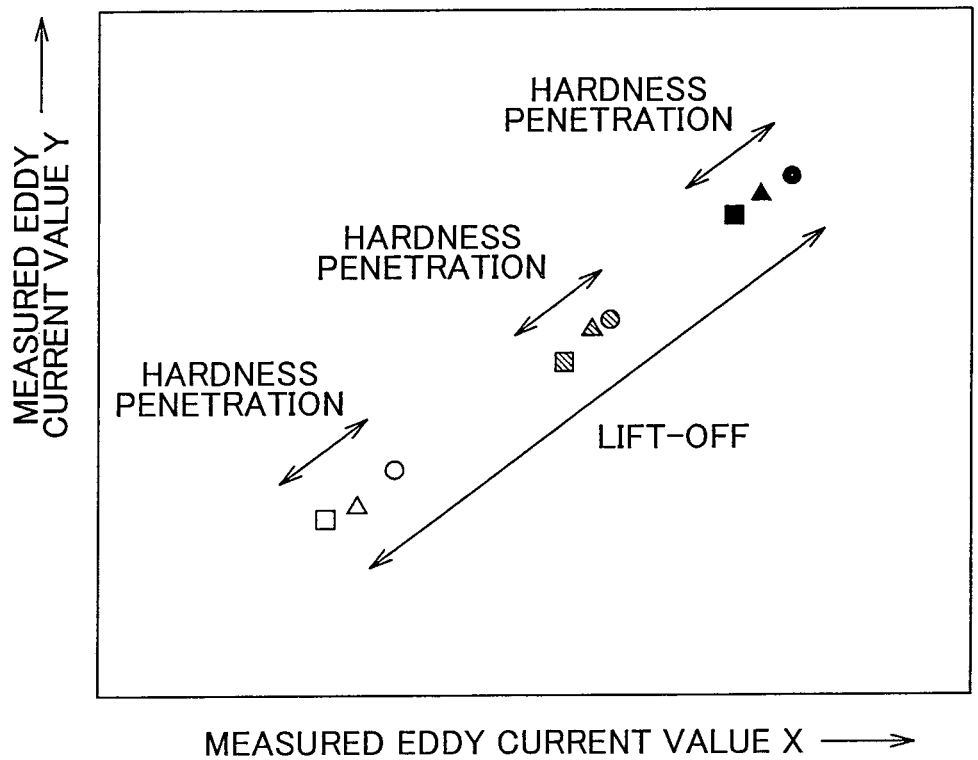
FIG. 16 is a graph that shows measured eddy current values detected by an eddy current sensor according to the related art.

When the thus configured eddy current sensor is used to measure the hardness penetration of a hollow work piece W that is a measurement object component, the probe 430 is inserted in the work piece W as shown in FIG. 15B. Then, alternating-current voltage is applied to each of the first excitation coil 451 and the second excitation coil 452 as an alternating-current excitation signal in a state where the probe 430 is arranged in proximity to the work piece W in position such that the detection coils 461 and 462 face the inner peripheral surface of the work piece W. Then, a magnetic field is generated in the work piece W.

At this time, horizontal magnetic fields that are horizontal to the respective detection coils are generated by the first excitation coil 451 and the second excitation coil 452 at portions facing the detection coils 461 and 462. Then, electromagnetic induction is caused by the horizontal magnetic fields, and eddy currents are generated in the work piece W that is a magnetic material through the electromagnetic induction. Furthermore, with the generation of eddy currents at the surface of the work piece W, induced voltages generated by the eddy currents are detected by the detection coils 461 and 462 as detection signals, and the computing unit calculates the detection signals as measured eddy current values to thereby measure the hardness penetration of a quenched portion WQ of the work piece W on the basis of the measured eddy current values.

In the present embodiment, as described above, the horizontal magnetic field of which the attenuation of the magnetic field strength due to lift-off is small is used for eddy current measurement, so the hardness penetration measurement test is less influenced by lift-off. Furthermore, the detection coils 461 and 462 are arranged at both intersecting portions of the first excitation coil 451 and the second excitation coil 452. By so doing, for a hollow work piece W as well, it is possible to measure the hardness penetration using the horizontal magnetic fields at the same time.

The invention claimed is:

1. An eddy current sensor comprising:
a probe that has an exciting portion configured to apply a predetermined alternating-current excitation signal to a measurement object component, the exciting portion including a first excitation coil that is arranged so that a center axis direction of the first excitation coil is oriented in a first axis direction and a second excitation coil that is arranged to intersect with the first excitation coil so that a center axis direction of the second excitation coil is oriented in a second axis direction perpendicular to the first axis direction, and a detecting portion configured to detect a detection signal generated in the measurement object component owing to the applied alternating-current excitation signal, the detecting portion including a detection coil that is arranged at one of two intersecting portions of the first excitation coil and the second excitation coil;
a computing unit configured to calculate the detection signal as a measured eddy current value, and
a controller configured to apply an alternating-current voltage to each of the first excitation coil and the second excitation coil as the alternating-current excitation signal in a state where the probe is arranged in proximity to the measurement object component in position such that the detection coil faces a measured portion of the measurement object component, to generate a first magnetic field in the first axis direction and a second magnetic field in the second axis direction at a portion of the measurement object component, facing the detection coil, to generate eddy currents by the first and second magnetic fields, to obtain induced voltages generated by the eddy currents as the detection signal, the induced voltages being detected by the detection coil of the detecting portion, and to measure a hardness penetration of the portion of the measurement object component, facing the detection coil, on the basis of the measured eddy current value calculated by the computing unit from the detection signal, wherein
the detecting portion includes one or two quenching determination coils that are arranged adjacent to the detection coil on one side or both sides in the first axis direction, and wherein
the controller applies the alternating-current voltage to each of the first excitation coil and the second excitation coil as the alternating-current excitation signal in a state where the probe is arranged in proximity to the measurement object component in position such that the detection coil and each quenching determination coil face the measured portion of the measurement object component, generates a magnetic field in a direction perpendicular to the first axis direction and the second axis direction at a portion of the measurement object component, facing each quenching determination coil, generates eddy current by the magnetic field, obtains induced voltage generated by the eddy current as a detection signal, the induced voltage being detected by each quenching determination coil of the detecting portion, and to determine whether the portion of the measurement object component, facing each quenching determination coil, is quenched or not quenched on the basis of the measured eddy current value calculated by the computing unit from the detection signal of each quenching determination coil of the detecting portion.

2. The eddy current sensor according to claim 1, wherein the detecting portion includes one or two perpendicular quenching determination coils, each of which is arranged perpendicularly to each quenching determination coil on an opposite side of the corresponding quenching determination coil with respect to the detection coil, and the controller applies alternating-current voltage to each of the first excitation coil and the second excitation coil as the alternating-current excitation signal in a state where the probe is arranged in proximity to the measurement object component in position such that the detection coil and each quenching determination coil face the measured portion of the measurement object component and each perpendicular quenching determination coil faces an upright portion that is perpendicular to the measured portion of the measurement object component to generate a magnetic field in the first axis direction at the upright portion of the measurement object component to thereby generate eddy current by the magnetic field, obtains induced voltage generated by the eddy current as the detection signal, the induced voltage being detected by each perpendicular quenching determination coil, and determines whether the portions of the measurement object component, respectively facing each quenching determination coil and each perpendicular quenching determination coil, is quenched or not quenched on the basis of the measured eddy current values calculated by the computing unit from the detection signal of each quenching determination coil and the detecting signal of each perpendicular quenching determination coil of the detecting portion.

3. An eddy current sensor comprising:
a probe that has an exciting portion configured to apply a predetermined alternating-current excitation signal to a measurement object component, the exciting portion including a first excitation coil that is wound so that a center axis direction of the first excitation coil is oriented in the first axis direction, a second excitation coil that is wound to intersect with the first excitation coil so that a center axis direction of the second excitation coil is oriented in a second axis direction perpendicular to the first axis direction, and a third excitation coil and a fourth excitation coil, that are wound to intersect with the first excitation coil so that center axes directions of the third excitation coil and fourth excitation coil are oriented in directions perpendicular to the first axis direction and inclined equally with respect to the second axis direction, and a detecting portion configured to detect a detection signal generated in the measurement object component owing to the applied alternating-current excitation signal, the detecting portion including a first detection coil that is arranged at one of two intersecting portions of the first excitation coil and the second excitation coil, a second detection coil that is arranged at one of two intersecting portions of the first excitation coil and the third excitation coil, adjacent to the first detection coil, and a third detection coil that is arranged at one of two intersecting portions of the first excitation coil and the fourth excitation coil, adjacent to the first detection coil;
a computing unit configured to calculate the detection signal as a measured eddy current value, and that is formed in a prismatic shape of which an axis is oriented in a first axis direction,
and
a controller configured to apply alternating-current voltage to each of the first excitation coil, the second excitation coil, the third excitation coil and the fourth excitation coil as the alternating-current excitation signal in a state where the probe is arranged in proximity to the measurement object component in position such that the first detection coil faces a measured portion of the measurement object component to generate magnetic fields in the measurement object component to thereby generate eddy currents by the magnetic fields, to obtain induced voltages generated by the eddy currents as detection signals, the induced voltages being detected by the first detection coil, the second detection coil and the third detection coil of the detecting portion, and to measure hardness penetrations of the portions of the measurement object component, respectively facing the first, second and third detection coils, on the basis of the measured eddy current values calculated by the computing unit from the detection signals.

4. An eddy current sensor that comprising:
a probe that has an exciting portion configured to apply a predetermined alternating-current excitation signal to a hollow measurement object component, the exciting portion including a first excitation coil that is arranged so that a center axis direction of the first excitation coil is oriented in a first axis direction and a second excitation coil that is arranged to intersect with the first excitation coil so that a center axis direction of the second excitation coil is oriented in a second axis direction perpendicular to the first axis direction, and a detecting portion configured to detect a detection signal generated in the hollow measurement object component owing to the applied alternating-current excitation signal, the detecting portion including two detection coils that are arranged at both intersecting portions of the first excitation coil and the second excitation coil;
a computing unit configured to calculate the detection signal as a measured eddy current value,
and
a controller configured to apply alternating-current voltage to each of the first excitation coil and the second excitation coil as the alternating-current excitation signal in a state where the probe is arranged in proximity to the hollow measurement object component in position such that the probe is inserted in the hollow measurement object component and the detection coils each face an inner peripheral surface of the hollow measurement object component to generate a first magnetic field in the first axis direction and a second magnetic field in the second axis direction at portions of the hollow measurement object component, facing the respective detection coils, to thereby generate eddy currents in the measurement object component by the magnetic fields, to obtain induced voltages generated by the eddy currents as detection signals, the induced, voltages being detected by the detection coils of the detection portion, and to measure hardness penetrations of the portions of the measurement object component, respectively facing the detection coils, on the basis of the measured eddy current values calculated by the computing unit from the detection signals.

5. An eddy current measurement method that uses the eddy current sensor according to claim 1 to measure a hardness penetration of a measurement object component, comprising:
preparing a plurality of preliminary measurement object components that have been subjected to quenching with known hardness penetrations one by one for each hardness penetration, setting a plurality of measurement distances between the eddy current sensor and each of the preliminary measurement object components at the time of quenching measurement over the preliminary measurement object components, detecting detection signals for the respective preliminary measurement object components for each measurement distance by the eddy current sensor, and calculating preliminary measured values $X0$ that serves as measured eddy current values in an X direction and preliminary measured values $Y0$ that serves as measured eddy current values in a Y direction on an X-Y coordinate plane from the detection signals for each hardness penetration and each measurement distance;
subjecting the preliminary measured values $X0$ and the preliminary measured values $Y0$ that are detected for each hardness penetration and each measurement distance to phase rotation on the X-Y coordinate plane to calculate preliminary rotation values $X1$ corresponding to the preliminary measured values $X0$ and preliminary rotation values $Y1$ corresponding to the preliminary measured values $Y0$, and, during the phase rotation, setting a phase rotation angle so that any one of the sets of preliminary rotation values $X1$ and the sets of preliminary rotation values $Y1$ is substantially constant when the hardness penetration is the same;
generating a hardness penetration calibration curve that indicates a correlation between the hardness penetration and the any one of the set of preliminary rotation values $X1$ and the set of preliminary rotation values $Y1$, which is made substantially constant in the preliminary rotation;

detecting a detection signal for the measurement object component by the eddy current sensor and calculating a measured eddy current value x0 in the X direction and a measured eddy current value y0 in the Y direction on the X-Y coordinate plane from the detection signal;

subjecting the measured eddy current value x0 and the measured eddy current value y0 to phase rotation on the X-Y coordinate plane at the same phase rotation angle as that of the phase rotation in the preliminary rotation to calculate a measured rotation value x1 corresponding to the measured eddy current value x0 and a measured rotation value y1 corresponding to the measured eddy current value y0; and measuring a hardness penetration of the portion of the measurement object component, facing the detection coil, from a correlation between the hardness penetration calibration curve and any one of the measured rotation value x1 and the measured rotation value y1.

6. The eddy current measurement method according to claim 5, further comprising:

before the preliminary measurement is executed, preparing a plurality of preliminary quenching measurement object components that are known to be quenched or not quenched, detecting detection signals for the respective preliminary quenching measurement object components by each quenching determination coil of the eddy current sensor, and calculating the detection signals as preliminary quenching measured values for each quenching determination coil; and calculating a quenching determination reference that indicates the preliminary quenching measured values for each quenching determination coil;

detecting a detection signal for the measurement object component by each quenching determination coil of the eddy current sensor and calculating the detection signal as a quenching measured eddy current value for each quenching determination coil;

comparing the quenching measured eddy current value and the quenching determination reference, both of which are calculated on the basis of the corresponding quenching determination coil, to determine whether the portion of the measurement object component, facing each quenching determination coil, is quenched or not quenched; and in the measurement, detecting the detection signal is by the eddy current sensor in the measurement object component that is determined in the quenching determination that all quenching determination portions are quenched and calculating the measured eddy current value x0 in the X direction and the measured eddy current value y0 in the Y direction on the X-Y coordinate plane from the detection signal.

7. An eddy current measurement method that uses the eddy current sensor according to claim 2 to measure a hardness penetration of a measurement object component, comprising:

preparing a plurality of preliminary quenching measurement object components, each of which has a measured portion and an upright portion perpendicular to the measured portion and is known to be quenched or not quenched, detecting detection signals at the measured portion and upright portion of each preliminary quenching measurement object component by each quenching determination coil and each perpendicular quenching determination coil of the eddy current sensor, and calculating the detection signals as preliminary quenching measured values for each quenching determination coil and each perpendicular quenching determination coil;

calculating a quenching determination reference that indicates the preliminary quenching measured values for each quenching determination coil and each perpendicular quenching determination coil;

preparing a plurality of preliminary measurement object components that have been quenched with known hardness penetrations one by one for each hardness penetration, setting a plurality of measurement distances between the eddy current sensor and each of the preliminary measurement object components at the time of quenching measurement over the preliminary measurement object components, detecting detection signals for the respective preliminary measurement object components for each measurement distance by the eddy current sensor, and calculating preliminary measured values X0 that serve as measured eddy current values in an X direction and preliminary measured values Y0 that serve as measured eddy current values in a Y direction on an X-Y coordinate plane from the detection signals for each hardness penetration and each measurement distance;

subjecting the preliminary measured values X0 and the preliminary measured values Y0 that are detected for each hardness penetration and each measurement distance to phase rotation on the X-Y coordinate plane to calculate preliminary rotation values X1 corresponding to the preliminary measured values X0 and preliminary rotation values Y1 corresponding to the preliminary measured values Y0, and, during the phase rotation, setting a phase rotation angle so that any one of the set of preliminary rotation values X1 and the set of preliminary rotation values Y1 is substantially constant when the hardness penetration is the same;

generating a hardness penetration calibration curve that indicates a correlation between the hardness penetration and the any one of the set of preliminary rotation values X1 and the set of preliminary rotation values Y1, which is made substantially constant in the preliminary rotation;

detecting a detection signal at the measured portion of the measurement object component by each quenching determination coil of the eddy current sensor and calculating the detection signal as a quenching measured eddy current value for each quenching determination coil;

detecting a detection signal at each upright portion of the measurement object component by each perpendicular quenching determination coil of the eddy current sensor and calculating the detection signal as a perpendicular quenching measured eddy current value for each perpendicular quenching determination coil;

comparing the quenching measured eddy current value and the quenching determination reference, both of which are calculated on the basis of the corresponding quenching determination coil, and comparing the perpendicular quenching measured eddy current value and the quenching determination reference, both of which are calculated on the basis of the corresponding perpendicular quenching determination coil, to determine whether the measured portion and upright portion of the measurement object component are quenched or not quenched;

detecting a detection signal by the eddy current sensor in the measurement object component that is determined in the quenching determination step that all the measured portions and upright portions are quenched and calculating a measured eddy current value x0 in the X direction and a measured eddy current value y0 in the Y direction on the X-Y coordinate plane from the detection signal;

subjecting the measured eddy current value x0 and the measured eddy current value y0 to phase rotation at the same phase rotation angle as that of the phase rotation in the preliminary rotation to calculate a measured rotation value x1 and a measured rotation value y1; and measuring a hardness penetration of the portion of the measurement object component, facing the detection coil, from a correlation between the hardness penetration calibration curve and any one of the measured rotation value x1 and the measured rotation value y1.

8. An eddy current measurement method that uses the eddy current sensor according to claim 3 to measure a hardness penetration of a measurement object component, comprising:

preparing a plurality of preliminary measurement object components that have been quenched with known hardness penetrations one by one for each hardness penetration, setting a plurality of measurement distances between the eddy current sensor and each of the preliminary measurement object components at the time of quenching measurement over the preliminary measurement object components, detecting detection signals for the respective preliminary measurement object components for each measurement distance by the eddy current sensor, and calculating preliminary measured values X0 that serve as measured eddy current values in an X direction and preliminary measured values Y0 that serve as measured eddy current values in a Y direction on an X-Y coordinate plane from the detection signals for each hardness penetration and each measurement distance;

subjecting the preliminary measured values X0 and the preliminary measured values Y0 that are detected for each hardness penetration and each measurement distance to phase rotation on the X-Y coordinate plane to calculate preliminary rotation values X1 corresponding to the preliminary measured values X0 and preliminary rotation values Y1 corresponding to the preliminary measured values Y0, and, during the phase rotation, setting a phase rotation angle so that any one of the set of preliminary rotation values X1 and the set of preliminary rotation values Y1 is substantially constant when the hardness penetration is the same;

generating a hardness penetration calibration curve that indicates a correlation between the hardness penetration and the any one of the set of preliminary rotation values X1 and the set of preliminary rotation values Y1, which is made substantially constant in the preliminary rotation;

detecting a detection signal for the measurement object component by the first detection coil of the eddy current sensor and calculating a first measured eddy current value x01 in the X direction and a first measured eddy current value y01 in the Y direction on the X-Y coordinate plane from the detection signal;

detecting a detection signal for the measurement object component by the second detection coil of the eddy current sensor and calculating a second measured eddy current value x02 in the X direction and a second measured eddy current value y02 in the Y direction on the X-Y coordinate plane from the detection signal;

detecting a detection signal for the measurement object component by the third detection coil of the eddy current sensor and calculating a third measured eddy current value x03 in the X direction and a third measured eddy current value y03 in the Y direction on the X-Y coordinate plane from the detection signal;

subjecting the first measured eddy current value x01, the first measured eddy current value y01, the second measured eddy current value x02, the second measured eddy current value y02, the third measured eddy current value x03 and the third measured eddy current value y03 to phase rotation at the same phase rotation angle as that of the phase rotation in the preliminary rotation to calculate a first measured rotation value x11, a first measured rotation value y11, a second measured rotation value x12, a second measured rotation value y12, a third measured rotation value x13 and a third measured rotation value y13 corresponding to the respective measured eddy current values;

measuring a hardness penetration of a portion of the measurement object component, facing the first detection coil, from a correlation between the hardness penetration calibration curve and any one of the first measured rotation value x11 and the first measured rotation value y11;

measuring a hardness penetration of a portion of the measurement object component, facing the second detection coil, from a correlation between the hardness penetration calibration curve and any one of the second measured rotation value x12 and the second measured rotation value y12; and measurement step of measuring a hardness penetration of a portion of the measurement object component, facing the third detection coil, from a correlation between the hardness penetration calibration curve and any one of the third measured rotation value x13 and the third measured rotation value y13.

* * * * *